United States Patent [19]

Tramontano et al.

[11] Patent Number: 5,030,717

[45] Date of Patent: * Jul. 9, 1991

[54] ANTIBODIES WHICH CATALYZE HYDROLYSIS OF ESTER BONDS

[75] Inventors: Alfonso Tramontano; Kim D. Janda, both of San Diego; Richard A. Lerner, La Jolla, all of Calif.

[73] Assignee: Scripps Clinic and Research Foundation, La Jolla, Calif.

[ * ] Notice: The portion of the term of this patent subsequent to Apr. 21, 2004 has been disclaimed.

[21] Appl. No.: 86,896

[22] Filed: Aug. 18, 1987

Related U.S. Application Data

[63] Continuation-in-part of Ser. No. 908,313, Sep. 17, 1986, abandoned, which is a continuation-in-part of Ser. No. 648,406, Sep. 7, 1984, Pat. No. 4,659,567.

[51] Int. Cl.$^5$ .................... A61K 39/395; C07K 15/21
[52] U.S. Cl. .................................. 530/387; 530/388; 530/391; 435/69.1; 435/70.21; 435/172.2; 435/240.27; 435/174; 435/197; 435/212
[58] Field of Search ............... 530/387, 389, 391, 806, 530/808; 424/85.8; 436/548; 435/68, 172.2, 240.27, 174, 197, 212

[56] References Cited

U.S. PATENT DOCUMENTS

| | | | |
|---|---|---|---|
| 4,659,567 | 4/1987 | Tramontano et al. | 530/387 |
| 4,792,446 | 12/1988 | Kim et al. | 530/387 |
| 4,888,281 | 12/1989 | Schochetman et al. | 530/387 |

OTHER PUBLICATIONS

Tramontano et al., *J. Am. Chem. Soc.*, 110:2282-2286 (1988).
Janda et al., *J. Am. Chem. Soc.*, 110:4835-4837 (1988).
Benkovic et al., *Proc. Natl. Acad. Sci. USA*, 85:5355-5358 (1988).
Janda et al., *Science*, 241:1188-1191 (1988).
White et al., *Principles of Biochemistry*, 6th ed. McGraw-Hill Bock Co., New York, 1978, pp. 980-982.
Lerner, Proc. XVIII th Solvay Conference on Chemistry, Van Binst, ed., Springer-Verlag, Berlin, 1986, pp. 43-49.
Jenks, *Catalysis in Chemistry and Enzymology*, McGraw-Hill, Inc., 1969, pp. 287 & 288.
Royer, *Adv. Catal.*, 29:197-227 (1980).
Jenks, *Adv. Enzymol.*, 43:219-411 (1975).
Lerner, *Adv. Imm.*, 36:1-44 (1984).
Tramontano et al., *Proc. Natl. Acad. Sci. USA*, 83:6736-6740, (1986).
Tramontano et al., *Science*, 234:1566-1570 (1986).
Pollack et al., *Science*, 234:1570-1573 (1986).
Napper et al., *Science*, 237:1041-1043 (1987).
Lerner et al., *TIBS*, 12:427-430 (1987).
Marx, *Science*:234:1497-1498 (1986).
Anon, Chemical & Engineering News, p. 6 (Dec. 16, 1986).
Hansen, *Nature*, 325:304 (Jan. 22, 1987).
Anon, *Scientific American*, 256:84-85 (Feb. 1987).
Baum, Chemical & Engineering News, pp. 30-33 (Apr. 6, 1987).
Stinson, Chemical & Engineering News, pp. 26—33 (Oct. 19, 1987).
Marx, *Science*, 241:1164 (1988).
Anon, Chemical & Engineering News, p. 14 (Sep. 5, 1988).
Vogel, *Discover*, 9:38-43 (Oct. 1988).
Kohen et al, Febs 111, 1980, pp. 427-431.
Kohen et al, *Biochem Biophys Acta* 629, 1980, p. 328.
Kohen et al, *FEBS* 100, 1979, p. 317.
Slobin, *Biochem* 5, 1966, pp. 2836-2844.
Kohler et al, *Nature*, 256, 1975, p. 495.

*Primary Examiner*—Esther L. Kepplinger
*Assistant Examiner*—Jeff Kushan
*Attorney, Agent, or Firm*—Dressler, Goldsmith, Shore, Sutker & Milnamow, Ltd.

[57] ABSTRACT

An analog-ligand having a conformation that substantially corresponds to the conformation of a hydrolytic transition state of an amide or ester reactant ligand is used to produce receptor molecules of predetermined specificity. The receptor molecules include an antibody combining site that binds to a reactant ligand and thereby stabilizes the tetrahedral carbon atom of the amide or ester hydrolysis transition state of that reactant ligand to catalytically hydrolyze the reactant ligand at a predetermined site.

18 Claims, 4 Drawing Sheets

FIG. 1
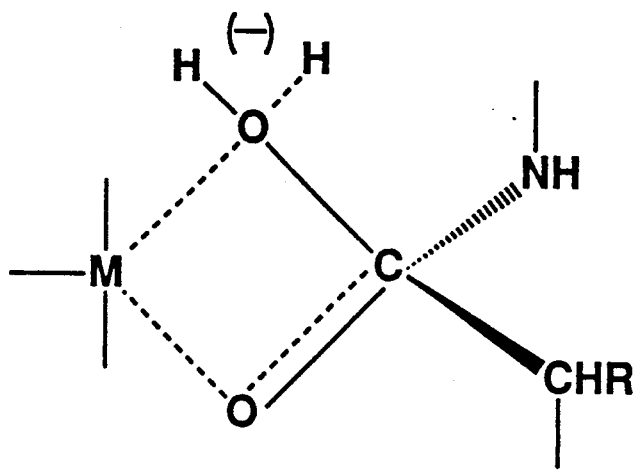
Fig. 1A
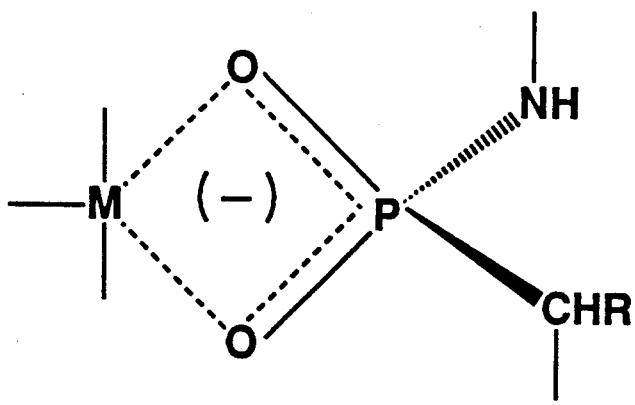
Fig. 1B

1,2

5

3,4

6

7-11

1

ANTIBODIES WHICH CATALYZE HYDROLYSIS OF ESTER BONDS

DESCRIPTION

This invention was made with the support of the United States Government, and the United States Government has certain rights in the invention.

CROSS-REFERENCE TO RELATED APPLICATION

This application is a continuation-in-part of copending application Ser. No. 908,313 filed on Sept. 17, 1986, now abandoned which is a continuation-in-part of its copending application Ser. No. 648,406 filed Sept. 7, 1984, now U.S. Pat. No. 4,659,567, the disclosures of both of which are incorporated herein by reference.

TECHNICAL FIELD

The present invention relates to antibodies, antigens and immunogens, and more particularly to molecules that contain an epitope that binds and thereby stabilizes the tetrahedral carbon atom of an amide or ester hydrolysis transition state and exhibits catalytic properties.

BACKGROUND OF THE INVENTION

Binding phenomena between ligands and receptors play many crucial roles in biological systems. Exemplary of such phenomena are the binding of oxygen molecules to deoxyhemoglobin to form oxyhemoglobin, and the binding of a substrate to an enzyme that acts upon it such as between a protein and a protease like trypsin. Still further examples of biological binding phenomena include the binding of an antigen to an antibody, and the binding of complement component C3 to the so-called CRl receptor.

Many drugs and other therapeutic agents are also believed to be dependent upon binding phenomena. For example, opiates such as morphine are reported to bind to specific receptors in the brain. Opiate agonists and antagonists are reported to compete with drugs like morphine for those binding sites.

Ligands such as man-made drugs, like morphine and its derivatives, and those that are naturally present in biological systems such as endorphins and hormones bind to receptors that are naturally present in biological systems, and will be treated together herein. Such binding may lead to a number of the phenomena of biology, including particularly the hydrolysis of amide and ester bonds as where proteins are hydrolyzed into constituent polypeptides by an enzyme such as trypsin or papain, or where a fat is cleaved into glycerine and three carboxylic acids, respectively.

Immunological binding may be used to experimentally divert binding interactions to catalytic processes. Jencks, W. P., *Catalysis in Chemistry and Enzymology*, page 288 (McGraw-Hill, New York 1969). Attempts to introduce reactive groups into a combining site of an antibody, however, have been unsuccessful. Royer, G. P., *Adv. Catal.*, 29, 197 (1980). Some monoclonal antibodies are reported to include nucleophilic residues which react with an activated ester appendage on a homologous hapten recognized by the antibody. Kohen et al., *FEBS Lett.*, 111, 427 (1980); Kohen et al., *Biochem. Biophys. Acta*, 629, 328 (1980) and Kohen et al., *FEBS Lett.*, 100, 137 (1979). In these cases, the rate of acylation of the nucleophile is presumably accelerated by its proximity to a binding site of the haptenic fragment.

These constructs, though interesting, are severely limited by the failure to address the mechanism of binding energy utilization which is essential to enzymes [W. P. Jencks, *Adv. Enzymol.*, 43, 219 (1975)]. Aside from this, when strong binding is directed to stable states, the slow rate of dissociation of the complex will impede catalysis. These deficiencies may be redressed by using a transition state analog as the hapten to elicit the desired antibodies. This hapten (also referred to herein as an "analog-ligand") can assume the role of an inhibitor in the catalytic system.

Hydrolysis of amide and ester bonds is thought by presently accepted chemical theory to proceed in aqueous media by a reaction at the carbonyl carbon atom to form a transition state that contains a tetrahedral carbon atom bonded to (a) a carbon atom of the acid portion of the amide or ester, (b) two oxygen atoms, one being from the carbonyl group and the other from a hydroxyl ion or water molecule of the medium, and (c) the oxygen atom of the alcohol portion of an ester or the nitrogen atom of the amine portion of an amide. Transition states of such reactions are useful mental constructs that by definition, cannot be isolated, as compared to intermediates, which are isolatable.

Although the above hydrolytic transition states can not be isolated, a large amount of scientific literature has been devoted to the subject. Some of that literature is discussed hereinafter.

Whereas the before-described transition state for amide and ester hydrolyses is believed to be well understood, the parameters of the topology, e.g., size, shape and charge, of receptor binding sites in which particular amides, such as proteins, or esters, such as fats, react through those transition states is not as well understood. It would therefore be beneficial if the topology of a plurality of binding sites were known so that the interactions of the ligands that bind in those sites could be studied. Unfortunately, the topology of receptor binding sites in biological hydrolyses is generally unknown, except for a relatively small number of enzymes whose X-ray crystal structures have been determined.

This lack of knowledge of binding site topology stems in part from a lack of knowledge of even the location in cells of many binding sites of receptors. In addition, for those receptor binding sites whose location is known, the chemical identity; i.e., protein and carbohydrate composition, of the binding site is generally unknown. Thus, the investigator is generally stymied in seeking to understand the topological requirements of receptor binding sites and therefore in seeking to construct therapeutic agents that can fulfill those requirements.

Investigators must therefore screen potential therapeutic agents in animal or cell culture studies to ascertain whether a potential therapeutic agent may be useful. Such systems, while useful, are expensive and time-consuming to use.

Even where the topology and chemical reactivity of a hydrolytic receptor such as an enzyme are known, enzymes such as hydrolytic proteases typically cleave their substrates, polypeptide chains, adjacent to a particular amino acid residue that may occur several times in the polypeptide chain of the protein. While such relatively random cleavage can be useful in obtaining a polypeptide map of the protein, that relatively random cleavage is not as useful where particular amino acid residue sequences are desired to be produced.

For example, modern genetic engineering techniques have been useful in preparing fusion proteins that contain a desired protein or polypeptide fused to the transcription product of a vector gene such as the lac z gene. The use of such fusion proteins is, however, hindered by the presence of fragments of the vector gene product. It would also therefore be beneficial if proteolytic enzyme-like molecules could be developed that would cleave such fusion products between the wanted and unwanted fusion polypeptide or protein portions.

Recently, Lerner, Tramontano and Janda [*Science*, 234, 1566 (1986)] reported monoclonal antibodies that catalytically hydrolyzed an ester. Tramontano and Lerner, also describe using monoclonal antibodies to hydrolyze esters in U.S. Patent No. 4,656,567. Pollack, Jacobs and Schultz [*Science*, 234, 1570 (1986)] reported a myeloma protein denominated MOPC167 [Leon et al., *Biochem.*, 10, 1424 (1971)] that catalyzes the hydrolysis of a carbonate.

In the two Lerner and Tramontano disclosures, the antibodies were raised to a phosphonate that was synthesized to represent a stable analog of the tetrahedral hydrolytic transition state of the carboxylic acid ester or carbonate ester. The Pollack et al. antibody principally discussed was a myeloma protein that happened to bind to a phosphonate that was structurally analogous to the carbonate analog hydrolyzed. Thus, in the Lerner and Tramontano et al. work, the substrate to be hydrolyzed was preselected, with the immunizing analog and hydrolytic antibodies being synthesized in accordance with the desired product. Pollack et al. designed the substrate to be hydrolyzed once they knew the specificity of the myeloma protein. Pollack et al. also reported (above) the existence of a catalytic antibody, substrated and analog substrate system for carbonate hydrolysis similar in concept to that of Lerner et al. Work relating to that system is reported in Jacobs et al., *J. Am. Chem Soc.*, 109, 2174 (1987).

Published patent application WO 85/02414 discusses the possible use of antibodies as catalysts, and presents data relating to the use of polyclonal serum in hydrolyzing o-nitrophenyl-beta-D-galactoside. The antibodies useful in that application are said to be inducible by a reactant, a reaction intermediate or to an analog of the reactant, product or reaction intermediate. The term "analog" is there defined to encompass isomers, homologs or other compounds sufficiently resembling the reactant in terms of chemical structure that an antibody raised to an analog can participate in an immunological reaction with the reactant but will not necessarily catalyze a reaction of the analog.

The data provided in that specification only indicate that some cleavage of the substrate (reactant) galactoside occurred over an eighteen hour time period using a relatively concentrated antibody preparation (1:10 and 1:20 dilutions). Although catalysis was alleged, catalytic activity was not shown since no turn over of the allegedly catalytic antibody was shown, nor was there an indication of the percentage of substrate galactoside cleaved. That application did indicate that beta-D-galactosidase cleaved about ten times as much substrate as did the polyclonal antibodies, presuming linearity of absorbance at the unnamed concentration of substrate studied.

From the data presented in that application, it is possible that a nucleophilic replacement of the o-nitrophenyl group occurred by a terminal amino group of a lysine residue of the antibody preparation used. Thus, the observed absorbance could have been due to formation of epsilon-amino lysinyl o-nitrophenyl aniline or to the formation of an epsilon-amino-lysinyl galactoside and o-nitrophenol, either of which occurrences would not be catalytic since the antibody was consumed, rather than turning over.

BRIEF SUMMARY OF THE INVENTION

The present invention contemplates a receptor molecule that contains an antibody combining site or idiotype-containing polyamide that is capable of catalytically hydrolyzing a preselected carboxylic acid and amide or ester bond of a reactant ligand. That antibody combinining site binds to (immunoreacts with): (a) a reactant ligand containing that preselected carboxylic acid amide or ester bond, and (b) a ligand analogous to the reactant ligand that contains a tetrahedrally bonded atom such as a phosphorus atom at a position analogous to that of the carbonyl carbon atom of the preselected carboxylic acid amide or ester bond of the reactant ligand. The hydrolytic transition state of the reactant ligand so bound contains a tetrahedral carbon atom bonded to (a) a carbon atom, the alpha-carbon of the acid portion of the ester or amide, (b) two oxygen atoms, and (c) the oxygen atom of an ester or the nitrogen atom of an amide.

Molecules containing an idiotype raised to the hydrolytic transition state of a reactant ligand are raised or induced by immunizing with analog-ligand molecules (preferably bound to a protein carrier to form a conjugate) containing an analog of a hydrolytic transition state of the ligand. The immunizing analog-ligand hydrolytic transition state molecule contains a tetrahedrally bonded central atom, such as phosphorus, bonded directly to (a) a carbon atom of the acid portion of the analogous ligand amide or ester, (the alpha-carbon of the acid portion) (b) two oxygen atoms and (c) a third oxygen atom or a nitrogen atom, the third oxygen atom or nitrogen atom being bonded to the alpha-carbon atom of an analogous ester or amide of the ligand.

The alpha-carbon atom of the acid portion, (a) above, bonded directly to the central tetrahedral such as phosphorus atom of the analog-ligand molecule, is included in a chain that contains at least 5 atoms, and more preferably at least about 15 atoms and including a substituted phenyl group, as is the third oxygen or nitrogen atom, (c) above. Of the two oxygen atoms, (b) above, bonded directly to the central atom, one oxygen atom (i) is bonded twice (doubly bonded) in an oxo group to the central atom, (ii) is part of an hydroxyl group or (iii) is the oxygen of an alkoxy group containing a $C_1$–$C_4$ lower alkyl group. The second of those oxygen atoms bonded to the central atom is singly bonded to the central atom and is an —$OR_2$ group, wherein $R_2$ is selected from the group consisting of hydrogen (H), and $C_1$–$C_4$ lower alkyl. The fourth atom, (c) above, bonded to the central atom of the analog-ligand molecule is the alcohol oxygen atom of an ester or the amine nitrogen atom of an amide of the analogous ester or amide portion of the ligand. That fourth atom is a portion of a chain that contains at least 5, and more preferably at least 15 atoms, and with the remainder of the chain constitutes $R_3$.

The tetrahedrally bonded central atom can be silicon, but is preferably phosphorus so that the analog-ligand is an organophosphorus compound with an arrangement of substitutents about the phosphorus that corresponds to the tetrahedral carbon transition state. A phosphonate monoacid in its ionized form also simulates the developing charge in nucleophilic attack at a carbonyl center. Moreover, phosphonamidate and phosphoramidate inhibitors of enzymic peptide hydrolysis have been described as mimics of transition states. Galardy et al., *Biochemistry*, 22, 1990 ((1983); Bartlett et al., *Biochemistry*, 22, 4618 (1983); Thorsett et al., *Proc. Natl. Acad. Sci. USA*, 79, 2176 (1982); Jacobsen et al., *J. Am. Chem. Soc.*, 103, 654 (1981); Kam et al., *Biochemistry*, 18, 3032 (1979) and Weaver et al., *J. Mol. Biol.*, 114, 119 (1977).

In one embodiment of this invention, monoaryl phosphonate esters, that function as transition state analogs in the hydrolysis of carboxylic acid esters, were synthesized and used as analog-ligands to produce specific monoclonal antibodies. Some of these antibodies react with particular aryl carboxylic esters to release a fluorescent alcohol. The reaction appears to be stoichiometric; however, the activity is regenerated under alkaline conditions or by treatment with a nucleophile such as hydroxylamine, and can therefore be said to be catalytic.

Some exemplary antibodies (receptors) react only with carboxylic acid esters containing the p-trifluoroacetamide substituent that is similarly disposed in the phosphonate analog-ligand. The analogous carboxylic acid ester with an acetamido group in this position does not function as a substrate. Saturation kinetics were observed for those receptors and kinetic parameters at low pH values are reported herein. Initial velocities indicate a more rapid reaction above pH 8. The phosphonate analog-ligand is a competitive inhibitor of the reaction ($K_i=35$ nM); whereas the carboxylate product of ester hydrolysis is a less effective inhibitor ($K_i=7000$ nM). Chemical modification of side chain groups in the antibody protein shows a partial reduction in activity on acylation of lysine or nitration of tyrosine, and a dramatic quenching upon modification of histidine.

Other exemplary receptors catalyze hydrolysis of both of the above-mentioned reactant ligands. Among those latter receptors, reactant ligand specificity can be relatively varied while still providing catalytic hydrolysis.

The results are discussed in terms of a mechanism in which amino acid residues of the antibody combining site participate in nucleophilic and/or general base catalysis. The properties of some of the exemplary antibodies of the present invention suggest that the catalytic hydrolysis mechanism is an example of enzymic transacylation where a deacylation step is rate limiting, and the results obtained demonstrate that enzymic function can be derived from immunological specificity.

It is thus to be appreciated that the invention, in a broader sense, contemplates reactant ligands and analog-ligands containing an analog to the hydrolytic transition state of the reactant ligand. Those molecules differ in the fact the reactant ligand contains a carbonyl group of an amide or ester whereas the ligand-analog contains a non-carbon central atom such as phosphorus. The reactant ligand and analog-ligand can also differ in the substitution of the two oxygen atoms (b) bonded to the central atom since the analog-ligand must possess sufficient stability to be used as a hapten, whereas the transition state mimicked by the analog-ligand cannot be isolated. Still further, although an antibody combining site is capable of exhibiting exquisite specificity, the structure of a reactant ligand can be varied while maintaining catalytic hydrolysis.

In the studies described herein, phosphonate monoaryl amides and esters function as transition state analogs to generate antibodies that are preferably monoclonal and that are aryl carboxylic esterases. In effect, these antibodies express their inherent binding energy functionally, as true enzymes, to hydrolyze esters and classically, as antibodies, to bind antigens.

Exemplary immunizing analog-ligand molecules that contain an analog of a hydrolytic transition state are represented by the formulas:

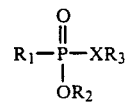

wherein
X=0 or NH;

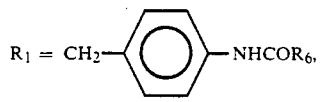

wherein
$R_6=CF_3$ or

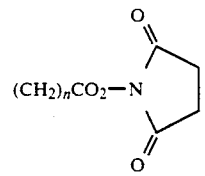

$R_2=$ H or $C_1$-$C_4$ lower alkyl; and

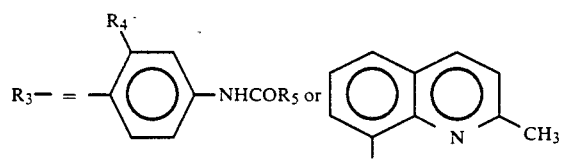

wherein

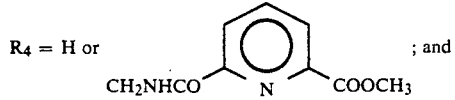

; and

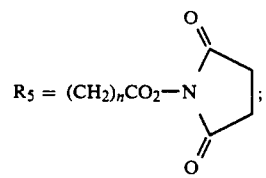

and n is an integer from 1 to 8 inclusive. The analog-ligand hydrolytic transition state molecules are themselves ligands, albeit not reactive ligands, and are also contemplated in this invention. These ligand molecules are of relatively small molecular size and are therefore typically linked to a larger, carrier molecule when used as immunogens to induce production of receptor molecules or are used alone as an inhibitor molecule. Such relatively small molecules are commonly referred to as haptens. These analog-ligand molecules also typically contain a linking atom or group such as a reactive mercaptan, a succinimide or other group that provides a means to attach the haptenic analog-ligand molecules to carriers for use as immunogens.

Exemplary reactant ligand molecules that structurally correspond to the foregoing analog-ligand molecules are represented by the formula:

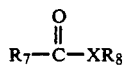

wherein
X=O;

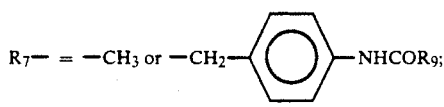

wherein $R_9$ is $CH_3$ or $CF_3$;

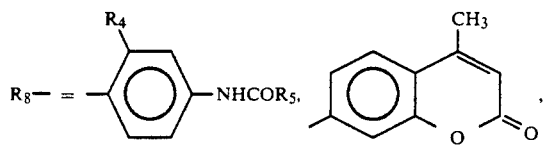

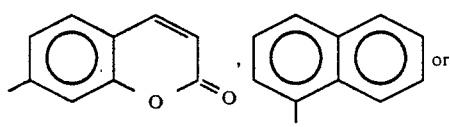

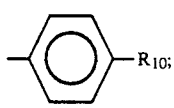

wherein $R_4$, $R_5$ and n are as described before; $R_{10}$=H, $NHCOR_{11}$,
wherein $R_{11}$=$C_1$-$C_6$ lower alkyl or substituted $C_1$-$C_6$ lower alkyl such as halo or carboxy alkyl.

The antibody combining site-containing molecules of the present invention are themselves receptors and provide information on the conformational preferences of antibody-hapten interactions through study of the intramolecular reactivity patterns of receptor-ligand complexes that are formed between the antibody combining site-containing molecules (receptors) and ligands of differing structures that contain similar or identical epitopic regions.

A method of preparing polyclonal receptor molecules that bind to the hydrolytic transition state of a particular amide or ester is also contemplated. Here, a before-described haptenic analog-ligand molecule containing a hydrolytic transition state analog is provided linked to a carrier as an immunogenic conjugate. The conjugate thus provided is dissolved or dispersed in a physiologically tolerable diluent to form an inoculum. The inoculum is introduced as by injection into a mammalian host in an amount sufficient to induce antibodies to the haptenic analog-ligand. The antibodies so induced are harvested. The harvested antibodies that immunoreact with the immunizing, haptenic analog-ligand are then collected.

In particularly preferred practice, monoclonal antibodies are prepared. Here, the above immunizing technique is used and the harvested antibodies are assayed for their ability to bind to (immunoreact with) the immunizing, haptenic ligand analog. Immunoglobulin-producing cells such as those from the spleen of an animal whose antibodies bind to the immunizing, haptenic analog-ligand are collected and are fused with myeloma cells to form hybridoma cells. The hybridoma cells are grown in a culture medium and the supernatant medium from the growing hybridoma cells is assayed for the presence of antibodies that bind to the immunizing, haptenic analog-ligand. Hybridoma cells whose supernatant contains such binding antibodies are then cloned to provide the desired monoclonal antibodies from culture medium supernatant or from the ascites of a host mammal into which the hybridoma is introduced.

The described polyclonal or monoclonal antibodies can be used as the receptors of this invention. Alternatively, the so-called Fc or Fc' portions of the antibodies can be removed as by enzymic cleavage to provide an antibody combining site (idiotype-containing polyamide) that binds to the immunizing, haptenic analog-ligand such as Fab or F(ab')$_2$ antibody portion, respectively.

The polyclonal, monoclonal and idiotype-containing polyamide receptors also bind to the hydrolytic transition state of the amide or ester ligand. Such binding typically leads to catalyzed hydrolysis of the reactant ligand.

The present invention provides several benefits and advantages. One benefit is the preparation of receptors whose binding site topological requirements are tailored to a particular ligand to be studied.

Another benefit of the present invention is the preparation of receptors that hydrolyze the amide or ester ligand at a predetermined site and which exhibit catalytic properties.

An advantage of the invention is that because of the specificity of the receptors that can be produced, a ligand containing a plurality of different hydrolyzable bonds such as a polypeptide or protein may be hydrolyzed at a preselected, particular hydrolyzable bond.

Yet another advantage of the present invention is the provision of receptors that bind to the hydrolytic transition state of a particular, preselected ligand, and exhibit catalytic properties thereby providing a means for studying the catalytic hydrolysis reaction of that ligand.

Still further benefits and advantages of the present invention will be apparent to those skilled in the art from the disclosures that follow.

BRIEF DESCRIPTION OF THE DRAWINGS

In the drawings, which constitute a portion of this disclosure:

FIG. 1A illustrates a proposed structure of the transition state in metallopeptidases. The bidentate coordination of the partially hydrated amide to the metal ion is one model for a stabilizing interaction that has been proposed to occur in the mechanism of peptide cleavage by a zinc peptidase. The model shown is supported by recent evidence suggesting that the zinc ion can become pentacoordinate in thermolysin, thereby simultaneously polarizing the carbonyl bond and delivering the nucleophilic water molecule. Monzingo et al., *Bio-* chemistry, 23, 5724 (1984); Hangauer et al., Biochemistry, 23, 5730 (1984)].

FIG. 1B illustrates the interactions of a phosphonamidate analog with a metalloenzyme which allow it to simulate the transition state configuration according to the model shown.

Figure 2:
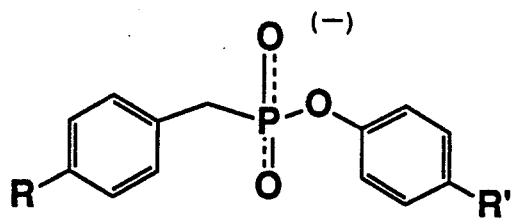
Figure 2:
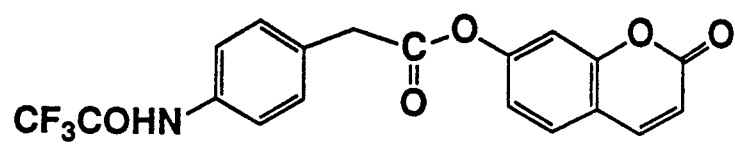
Figure 2:
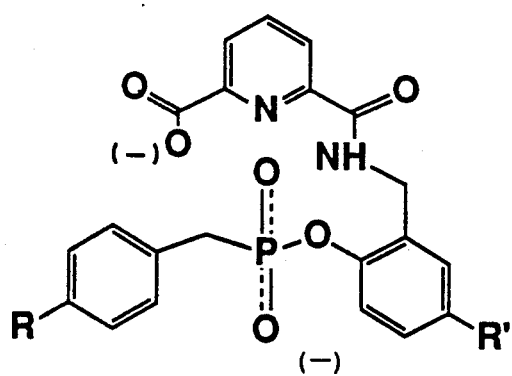
Figure 2:
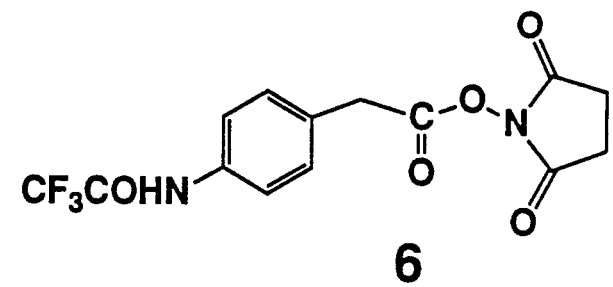
Figure 2:
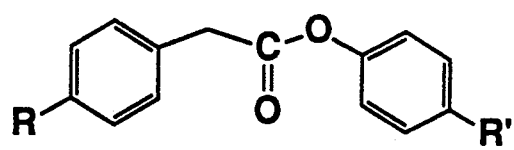

FIG. 2 illustrates the analog-ligands and ligands used in the production and assay of monoclonal antibodies with esterolytic properties. The identity of substituents R and R' are as follows: Compounds 1/ and 7: R=NHCOCF$_3$, R'=NHCOCH$_3$; Compounds 2 and 4: R=NHCOCF$_3$, R'=NHCO(CH$_2$)$_4$COON(COCH$_2$)$_2$; Compound 8: R=NHCOCF$_3$, R'=NHCO(CH$_2$)$_2$COOH; Compound 9: R,R'=NHCOCH$_3$; Compound 10: R=NHCOCF$_3$, R'=H; Compound 11: R=NHCOCH$_3$, R'=NHCOCF$_3$.

Figure 3:
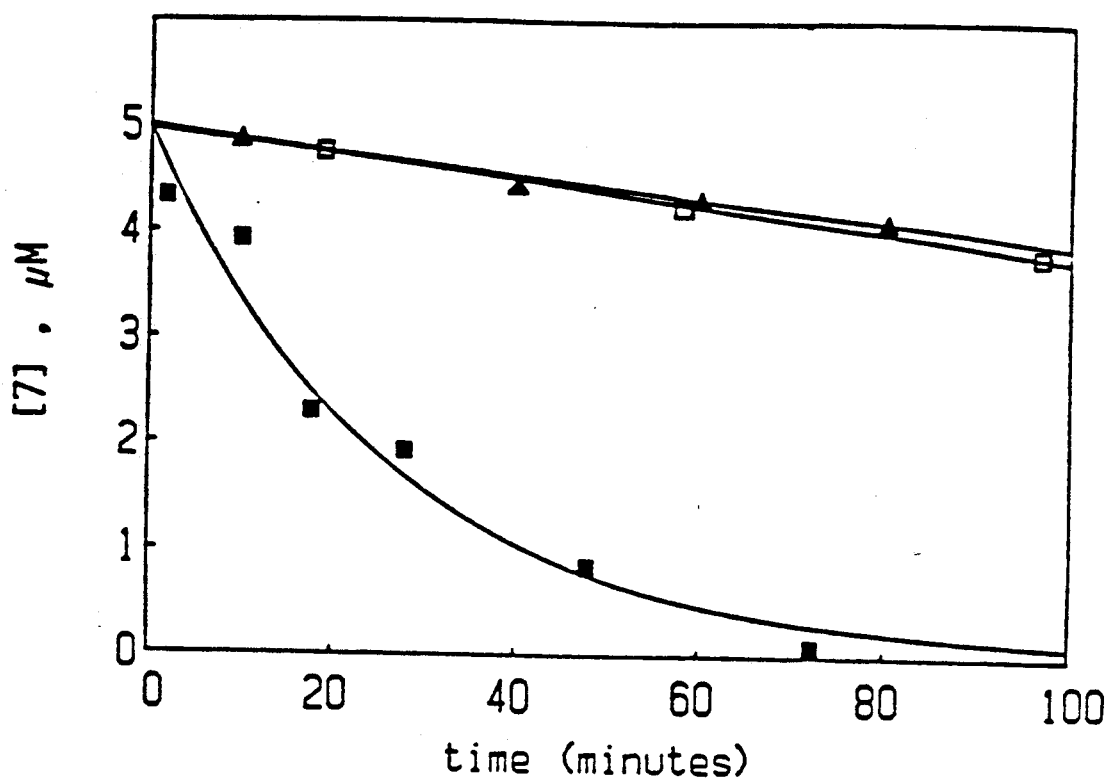

FIG. 3 illustrates the rate of hydrolysis of a carboxylic ester (Compound 7) determined by HPLC under the conditions described in Table 1 (50 mM phosphate buffer at pH 8.0 and 23 degrees C). ▲ Uncatalyzed (background) rate of hydrolysis. (□) Effect of 0.5 micromolar non-specific monoclonal IgG. ■ 0.1 Micromolar anti-Compound 4 monoclonal antibody from hybridoma P3 6D4. The superimposed curve represents a theoretical exponential decay which fits the data points.

Figure 4:
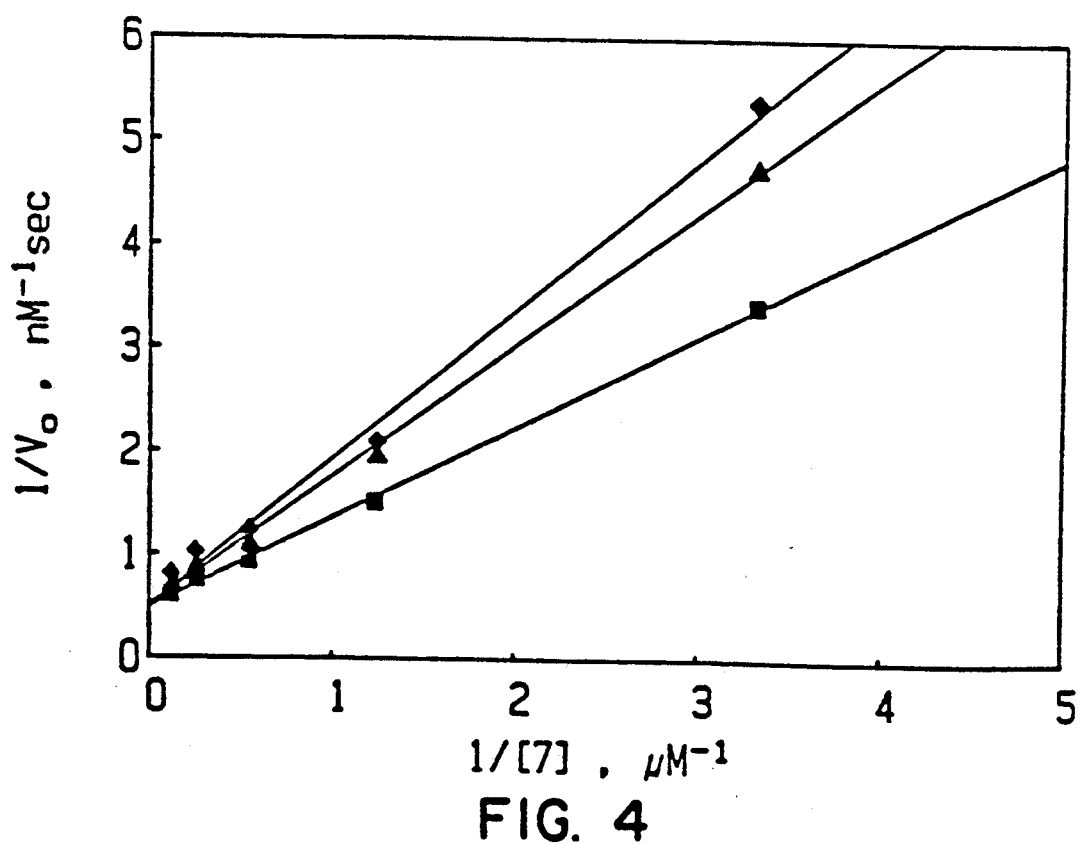

FIG. 4 illustrates a Lineweaver-Burk plot for the hydrolysis of Compound 7 by anti-Compound 4 monoclonal antibody from hybridoma P3 6D4. Velocities were determined spectrophotometrically by measuring initial rates during the first linear portion of the reaction as described with reference to Table 2. The substrate concentrations were corrected for amounts consumed during initial equilibration. ■ No inhibitor present. ▲Inhibited by 50 (Compound 3). ◆ Inhibited by 100 nM phosphonate (Compound 3).

Figure 5:
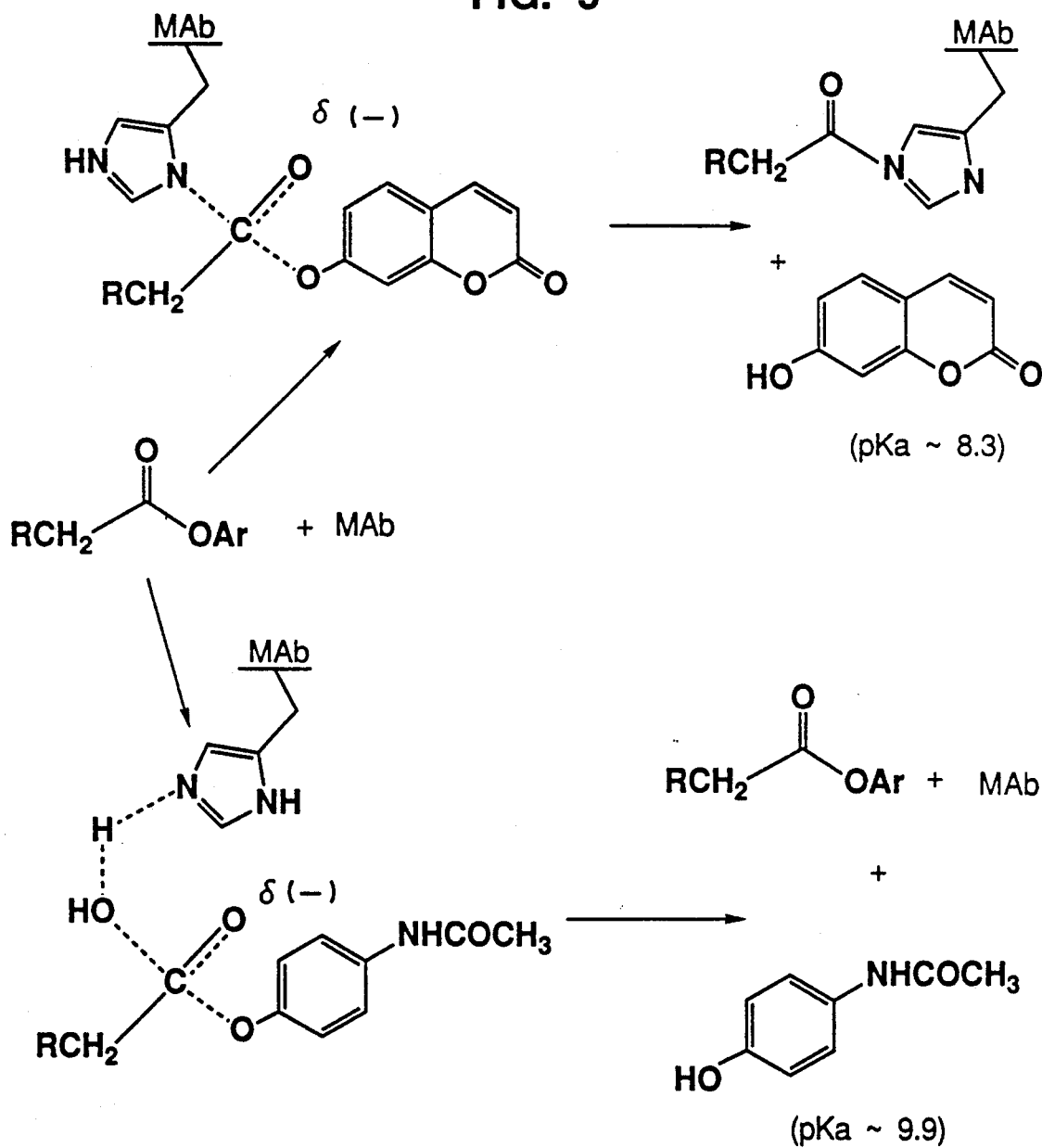

FIG. 5 illustrates a proposed scheme that accounts for the divergent chemistry observed in the reaction of an anti-Compound 4 monoclonal antibody with different carboxylic esters (Compound 5 and Compound 7). A histidine residue in the combining site is presumed to act as a nucleophilic (upper pathway) or general base (lower pathway) catalyst during the formation and breakdown of a tetrahedral intermediate. The ester with a good leaving group reacts by the upper pathway since the rate-limiting step, formation of the intermediate, is facile. This pathway is precluded for the ester with a poor leaving group since the rate-limiting step, breakdown of the intermediate, is not catalyzed relative to the analogous step in the lower pathway, which may be general-base catalyzed.

DETAILED DESCRIPTION OF THE INVENTION

I. Introduction

The present invention relates to molecules collectively referred to as receptors that are antibodies and idiotype-containing polyamide (antibody combining site or paratopic) portions induced by an analog of a reactant ligand that mimics the conformation of transition state in the reaction sequence for the hydrolysis of an ester or an amide. The receptor molecules (antibodies and idiotype-containing polyamides) bind to the analog-ligand and to the reactant ligand, and are thought to stabilize the hydrolytic transition state of a preselected portion of the reactant ligand, and thereby exhibit catalytic properties as to the reactant ligand.

The work described herein discusses twelve monoclonal receptor molecules, each of which is capable of catalytically hydrolyzing one or more reactant ligands. Those receptors molecules were induced by immunizations with different analog-ligands. Thus, the generality of the invention in making and using antibody catalysts for hydrolytic cleavage of reactant ligands corresponding in structure to the described analog-ligands has been illustrated.

Antibodies and enzymes are both proteins whose function depends on their ability to bind specific target molecules. Enzymatic reactions differ from immunological reactions in that in an enzymatic reaction the binding of the enzyme to its substrate typically leads to chemical catalysis, whereas a non-catalytic complex is the usual result of antibody-antigen binding.

Enzymes are believed to catalyze the hydrolysis of proteins by combining with the protein to stabilize the transition state of the hydrolysis reaction. It is generally believed that the rate of an enzymatic reaction is increased relative to the rate of a non-enzymatic reaction because of the ability of the enzyme to stabilize the transition state of the reaction; i.e., to reduce the free energy of the transition state, and thus, the free energy of activation, of the reaction [Jencks, W. P., Adv. Enzymology, 43, 219 (1975) and Pauling, L., Amer. Scientist, 36, 58 (1948)]. Support for this theory comes from the observation that substances that are thought to model the presumed transition states are often strongly bound to the enzymes as competitive inhibitors. Leinhard, G., Science, 180, 149 (1973) and Wolfenden, R., Acc. Chem. Res., 5, 10 accomplishes this lowering of the reaction free energy by binding the transition state geometry of the reactant more strongly than it binds to the corresponding substrate(s) or product(s).

This means that the intrinsic binding energy of the enzyme is much greater than can be measured from the binding of substrates or products. Essentially, the binding energy of the enzyme is utilized to perform the chemical reaction [Jencks, W. P., XVII International Solvay Conference (November 1983)].

The converse proposition is that a receptor that is prepared to optimally bind a suitable analog of a transition state would function as a catalyst. The demonstration of this result completes the correlation of enzyme function and receptor structure and provide a useful approach to devising artificial enzymes.

The basic idea behind immunological hydrolysis described herein contemplates the use of analog-ligands in the preparation of antibodies of predetermined specificity that preferentially bind to and thereby stabilize the transition state of amide or ester bond hydrolysis upon binding to the specified reactant ligand. An analog-ligand simulates the conformation of a high energy transition state in hydrolysis to induce the production of antibodies having the ability to bind related substrates and stabilize their hydrolyses.

Such preferential binding and stabilization result in a reduction in the activation energy for the hydrolysis reaction, thus meeting a criterion for catalysis. Antibodies that display this property can be obtained by immunization with synthetic analogs that are chemically modified to resemble the bonding characteristics of a substrate reactant ligand undergoing bond hydrolysis; i.e., by immunization with transition state analogs of the particular reaction.

The mechanism by which an antibody hydrolyzes an ester or amide bond of a bound reactant ligand can be thought of in terms of an "induced fit" model. As the loosely bound substrate distorts or rearranges to conform to the binding geometry of the antibody, stress can be relieved by chemical reorganization of a single, predetermined amide or ester bond such that this reorganization leads to the hydrolysis of the bond.

The term "receptor" is used herein to mean a biologically active molecule that binds to a reactant ligand, inhibitor ligand, or analog-ligand. The receptor molecules of the present invention are antibodies, substantially intact antibodies or idiotype-containing polyamide portions of an antibody. Biological activity of a receptor molecule is evidenced by the binding of the receptor to its antigenic reactant ligand, inhibitor ligand or analog-ligand upon their admixture in an aqueous medium, at least at physiological pH values and ionic strengths. Preferably, the receptors also bind to an antigenic ligand within a pH value range of about 5 to about 9, and at ionic strengths such as that of distilled water to that of about one molar sodium chloride.

Idiotype-containing polyamide portions (antibody combining sites) of antibodies are those portions of antibody molecules that include the idiotype, and bind to the ligand or analog-ligand. Such portions include the Fab, Fab' and F(ab')$_2$ fragments prepared from antibodies by well-known enzymatic cleavage techniques. See for example, U.S. Pat. No. 4,342,566 to Theofilopoulos and Dixon, generally, and specifically, Pollack et al. [Science, 234, 1570 (1987)] who reported accelerated hydrolytic rates for Fab fragments were the same as those of the native Ig. Inasmuch as the antibodies from which idiotype-containing polyamides are obtained are described as raised against or induced by immunogens, idiotype-containing polyamide receptors are discussed as being "raised" or "induced" with the understanding that a cleavage step is typically required to obtain an idiotype-containing polyamide from an antibody. Intact antibodies are preferred, however, and are utilized as illustrative of the receptor molecules of this invention.

The receptors useful in the present invention are preferably monoclonal antibodies. A "monoclonal antibody" is a receptor produced by clones of a single cell called a hybridoma that secretes but one kind of receptor molecule. The hybridoma cell is fused from an antibody-producing cell and a myeloma cell or other self-perpetuating cell line.

Techniques for preparing the monclonal antibodies of the present invention are well known. Such receptors were first described by Kohler and Milstein, *Nature*, 256, 495 (1975), which is incorporated herein by reference. Monoclonal antibodies are typically obtained from hybridoma tissue cultures or from ascites fluid obtained from mammals into which the hybridoma tissue was introduced. Both methods are described herein.

Monoclonal receptors are preferred herein because of their unique specificity in binding to a particular epitope such as a particular immunizing analog-ligand and reactant ligand, as well as their relatively higher specific catalytic activity as compared to polyclonal antibodies. Polyclonal antibody preparations can also be used herein, but typically have to be separated into fractions that bind to the immunizing analog-ligand and those that bind to extraneous epitopes such as those of the antigenic carrier.

Polyclonal antibodies that bind to the analog-ligand can be separated by affinity separation using an analog-ligand as the affinity sorbant. After admixture and maintenance of an antibody preparation with the affinity sorbant for a time sufficient for appropriate immunoreaction to take place, the affinity sorbant is separated from the remaining portion of the antibody preparation.

The separated, remaining antibody portion bound to the affinity sorbant contains the antibodies that bind to the analog-ligand, whereas antibodies in the separated remaining portion of the antibody preparation bind to extraneous epitopes. Those affinity-bound antibodies can thereafter be isolated by usual techniques for separating bound entitites from affinity sorbants, such as washing the sorbant with glycine-hydrochloride at pH 2.

A ligand is defined herein as a molecule or complex that immunoreacts with or binds to a receptor molecule antibody combining site. Two types of ligand are contemplated herein. A first is termed an analog-ligand and is used as an immunogen to induce preparation of receptor molecules and as an inhibitor of the receptor molecule synthase-catalyzed reaction. The second is referred to as the ligand, reactant ligand or reactant ligand substrate and is the molecule that undergoes the catalyzed reaction. The analog-ligand is substantially inert to undergoing the catalyzed reaction.

As described herein, chemical analogs of amide or ester ligands have been synthesized that incorporate phosphonamidate or phosphonate moieties at specific, predetermined sites to mimic the conformation of the transition state in the hydrolysis of an amide or ester bond. Such analogs are suitable candidates for this investigation because it is known that phosphonamidates have been used as transition state analogs in the inhibition of proteolytic enzymes [Bartlett, et. al., *Biochemistry*, 22, 4618 (1983)].

Hydrolysis of the amide bond of polypeptides or proteins requires analog-ligands that are substantially free from hydrolysis when utilized as a haptenic immunogen. Phosphonamidates described for the inhibition of certain proteases (Bartlett et al., id. and Jacobsen et al, *J. Am. Chem. Soc.*, 103, 654 (1981) can also be modified for inducing the production of useful receptors herein.

Short polypeptide chains can induce the production of antibodies that recognize and bind to a homologous protein at a predetermined specific site. The present invention carries the earlier work with polypeptides a major step forward. Here, the antibodies (receptors) are induced by an immunizing haptenic first molecule (the analog-ligand), and recognize and bind not only to that first molecule, but also to a second, related molecule (the reactant ligand). In binding that second molecule, the receptor causes hydrolysis (which as demonstrated herein can be catalytic) of a preselected, ester or amide bond that corresponds in topology to the topology of the immunizing, haptenic first molecule. The correspondence in topology; i.e., size, shape and charge, provides a means for preselecting the site at which hydrolysis of the ligand occurs. Inhibitor ligands that resemble the structure of an analog-ligand or a reactant ligand are also bound by receptor molecules.

Consequently, by synthesis of a relatively small, immunizing haptenic analog-ligand, one can induce the production of receptor molecules that recognize, bind to and catalytically cleave an ester or amide bond in another molecule that can contain a plurality of amide or ester bonds. Thus, a receptor can be prepared that causes hydrolysis of a selected, predetermined amide bond of a protein or polypeptide such as the before-discussed genetically engineered fusion protein.

The implication of this result is that one can confer the activity of hitherto unknown proteases to immunoglobulins.

Furthermore, the activity of the antibody can be directed to any predetermined site at will by designating the amide or ester bond to be cleaved with the phosphonamidate or phosphonate configuration in the haptenic analog-ligand used for immunization. This is shown herein for the hydroxy coumarin esters where the exocyclic ester bond that corresponds to the phosphorus-containing bond of the analog-ligand is cleaved, whereas the endocyclic ester bond (lactone) of the hydroxycoumarin moiety that had no tetrahedral phosohorus-containing counterpart in the analog-ligand is not hydrolyzed.

Thus a method is described for the selective bond cleavage such as proteolysis of a protein whose local sequence conforms to that of the moleculecontaining bond (polypeptide) targeted. The applications of such a method in protein chemistry, biochemistry, and medicine are without limit.

The disclosure in our U.S. Pat. No. 4,659,567, which is incorporated herein by reference, relates in part to the hydrolysis of p-nitrophenyl and coumarinyl esters. Compounds were prepared to act as the transition state analogs of, for example, the corresponding p-nitrophenyl and coumarinyl carbon rather than phosphorus esters in an immunological study. For example, antibodies generated to a compound designated C1 bound to a protein carrier were isolated and screened in an assay for hydrolysis of the ligand ester that corresponds to analog-ligand Compound C1. The liberation of the fluorescent 4-methyl-umbelliferone molecule in that reaction was used to facilitate the detection of hydrolytically active antibodies. Such antibodies did in fact hydrolyze coumarin esters.

The antibodies and idiotype-containing polyamide portions of antibodies were induced by a haptenic ester or amide analog-ligand hydrolytic transition state molecule. The haptenic molecule, as defined in our patent, contains a tetrahedrally bonded central phosphorus or silicon atom bonded directly to (a) a carbon atom, (b) two oxygen atoms and (c) a third oxygen atom or a nitrogen atom, the third oxygen atom or nitrogen atom being bonded to a carbon atom (the alpha-carbon) of the alcohol or amine portion of an analogous ester or amide of the ligand.

The foregoing studies support the proposition that the simple binding of antibodies with ligands is amenable to chemical catalysis through the mechanism-based design of haptenic structures. The binding interaction directed to the phosphonate moiety helps to stabilize the transition state or tetrahedral intermediate, with which it has stereoelectronic similarity, in a transacylation reaction. The process, illustrated by the results described in that patent was not truly catalytic because it appears to result in acyl transfer to an essential residue of the antibody combining site, forming a stable acylated antibody. This result is unexpected since such a mechanism is not indicated in the design of the transition state analog. It is possible that the functional groups in or near the active hydrolytic site allow two alternate mechanisms for transacylation to compete and that the lowest energy pathway changes with the choice of substrate. The labile esters, which are useful for the assay to detect low levels of esterase activity, are likely to undergo acyl transfer to a nucleophilic group in the antibody.

The study of these chemically reactive monoclonal antibodies with more stable ligands has now demonstrated that highly specific esterase activity is expressed. Carboxylic esters that correlate to the structural features of the particular hapten used are accepted by the antibody in a catalytic process that exhibits many of the characteristics of an enzyme including specific inhibition by the transition state analog.

II. Transition State of Esterolysis and Hapten (Analog-Ligand) Design

Design of the analog-ligand flows backward from the structure of the product to be formed through the transition state for bond formation to be mimicked, and then to the analog-ligand. Reactions that involve amide or ester hydrolysis provide illustrative examples of the genereal concept and are utilized herein as exemplary for an ester or amide hydrolysis reaction.

Transacylation processes are characterized by carbonyl addition-elimination mechanisms. The acyl group may, therefore, possess varying degrees of tetrahedral character in this transition state. W. P. Jencks, *Catalysis in Chemistry and Enzymology*, ch. 10, (McGraw-Hill, New York, 1969). The enzymes that catalyze transacylation reactions might be expected to bind well those analogs of the reactant ligand having a tetrahedral configuration about the acyl center. This is true for serine proteases, where a covalent bond between the ligand (substrate) and the enzyme is formed temporarily [Westerik et al., *J. Biol. Chem.*, 247, 8195 (1972); R. C. Thompson, *Biochemistry*, 12, 47 (1973) and Imperali et al., *Biochemistry*, 25, 3760 (1986)], as well as for enzymes that catalyze the direct hydration of amides or esters. The latter category is inhibited by compounds with a tetrahedral configuration including a phosphate, phosphonate or phosphonamidate group in lieu of the scissile amide unit [Weaver et al., *J. Mol. Biol.*, 114, 119 (1977) and Jacobsen et al., *J. Am. Chem. Soc.*, 103, 654 (1981)].

Naturally occurring and synthetic substances containing phosphorus have been studied as inhibitors of metallopeptidases. In these enzymes, the transition state would appear to contain the hydrated amide in the coordination sphere of the metal ion [W. N. Lipscomb, *Acc. Chem. Res.*, 15, 232 (1982)]. A complete picture of a transition state analog might then have the phosphono group of an inhibitor as a ligand to a metal ion or some other polarizing site (see FIG. 1) [Weaver et al., *J. Mol. Biol.*, 114, 119 (1977) and Christianson et al., *J. Am. Chem. Soc.*, 108, 545 (1986)]. The role of the metal ions in metallopeptidases, however, is not clearly understood. It may have a multiple function in amide hydrolysis where proton transfer steps among the tetrahedral intermediates may be rate-limiting [L. M. Sayre, *J. Am. Chem. Soc.*, 108, 1632 (1986)].

The hydrolysis of carboxylic acid esters is a simpler example of transacylation that should also be approximated by the phosphonate-containing analog of the transition state. The binding of the charged phosphonate group may describe a stabilizing interaction in the transition state that would lead to catalysis. Ester hydrolysis reactions generally proceed at convenient spontaneous rates under ambient conditions that are suitable for antibodies. Therefore, any small rate acceleration can be readily detected.

The structures of the analog-ligands and reactant ligands for this investigation were selected according to certain criteria. These included the availability and stability of the organophosphorus precursors, the corresponding carboxylic acid substrate, the convenience of the chemical synthesis for its preparation, and the adaptability to diverse schemes for immunological presentation.

A basic molecular unit that provides the necessary features is the substituted aryl phenylacetic acid analog structures shown, for example, in Compounds 1-4 of FIG. 2. By including amino substituents in the aromatic rings, either the benzylic or phenolic group, for example, can be provided with a functional appendage for coupling to immunogenic carrier proteins for haptenic presentation. The structure also permits the incorporation of an additional appendage in the phenolic ring for the creation of a metal binding site. This structure is desirable for producing an antichelate antibody with the structural organization for a metaloesterase.

Such a possibility was investigated using a dipicolinic acid halide to derivatize the ortho aminomethyl group of a phenolic structure (see Compounds 3 and 4 and 4 of FIG. 2). The dealkylation of the phosphonyl and acyl esters of this adduct exposes the potential ligands for the formation of a metal chelate. The intrinsic stability of complexes of this ligand, however, determined with divalent transition metals such as cobalt, zinc and copper, are probably too low to expect these chelates to maintain their integrity in the immunization process. In fact, the formation constants of 1:1 chelates of Compound 3 with the divalent metal ions are in the range of $10^4$-$10^5$ $M^{-1}$ as estimated by titrimetric analysis. The possible use of more stable complexes, of trivalent cobalt, for example, to generate a stable haptenic chelate may provide more meaningful results.

Thus, the present invention generally relates to receptors, preferably monoclonal, that are capable of hydrolyzing a preselected amide or ester bond of a ligand whereby the receptors contain an antibody combining site that binds: (a) to a reactant ligand that can form the tetrahedral hydrolytic transition state of a preselected ester or amide bond of the reactant; i.e., contains a preselected carboxylic acid amide or ester bond, and (b) to an analog of the ligand having a tetrahedrally bonded phosphorus atom located at the position occupied by the carbonyl group carbon atom of the preselected ester or amide bond of the reactant ligand. The tetrahedrally bonded phosphorus atom is bonded directly to:

(i) carbon atom (the alpha-carbon) of the acid portion of the analogous reactant ligand ester or amide;

(ii) two oxygen atoms, one of which is bonded to the phosphorus atom by a double bond whereby the oxygen is an oxo radical, and the other of the two oxygen atoms is bonded singly to the phosphorus and singly to a radical selected from the group consisting of hydrogen and $C_1$-$C_4$ lower alkyl; and (iii) a third oxygen atom or a nitrogen atom that is bonded to a carbon atom of the analogous ester or amide; i.e., to alpha-carbon of the alcohol or amine portion of the ester or amide.

Where a cyclic amide or ester is the reactant ligand, there are not distinct acid and amine or alcohol portions of the molecule. However, those skilled in organic chemistry will understand that amides and esters must by definition contain acid and amine or alcohol portions. Thus, an imaginary line of demarcation can be drawn for such molecules that includes at least the carbonyl carbon and its directly bonded alpha-carbon in the acid portion of the molecule and includes the amino or hydroxyl group and its directly bonded alpha-carbon in the amine or hydroxyl portion of the molecule.

In another embodiment, this invention relates to a method of catalytically hydrolyzing a preselected ester or amide bond in reactant ligand molecule. The method comprises the steps of: (a) admixing an effective amount of one of the foregoing receptors with reactant ligand molecules in an aqueous medium; and (b) maintaining the admixture for a period of time sufficient for the ligand molecules to bind to the receptor and for the receptor molecules to hydrolyze the preselected bond. The products of that hydrolysis can be thereafter recovered, if desired.

A hydroltyic method of this invention utilizes an aqueous medium as a portion of the reaction admixture. That medium typically contains water and buffer salts. In addition, the medium can contain other salts such as sodium choride, as well as water-soluble calcium and magnesium salts as are frequently found in protein-containing media. Other water-soluble polyvalent metal salts such as iron, zinc and cobalt salts can also be present and are useful complexing agents where the reactant ligand is comprised of two separate molecules. Organic solvents such as methanol, ethanol, acetonitrile, dimethyl sulfoxide, dioxane, hexamethylphosphoramide and N,N-dimethylforamide can also be present. Surface active agents that emulsify the reactant ligand and receptor molecule can also be present. The critical feature of ingredients present in the aqueous medium is that those ingredients not substantially interfere with or inhibit the catalytic reaction as by denaturation of the receptor molecule. Additionally, the aqueous medium is substantially free from salt, proteins generally, and enzymes, specifically, that inhibit the bond-breaking reaction catalyzed by the receptor molecule.

The aqueous medium typically has a pH value of about 5 to about 9, and preferably about pH 6.0 to about 8.0. pH values greater and less than those recited values can also be utilized so long as the catalyzed reaction is again not substantially interfered with or inhibited.

The catalytic reactions are typically carried out at ambient room temperature; i.e., at about 20 to about 25 degrees C., and at an ambient atmospheric pressure. However, temperatures down to about the freezing point of the aqueous medium and up to about the boiling point of the medium at atmospheric pressure can also be used. As is known, proteins such as the receptor molecule tend to denature at elevated temperatures such as those at which an aqueous medium boils, e.g. at about 100 degrees C., and thus temperatures below about 40 degrees C. are preferred. As is also well known, reactions that follow multimolecular kinetic expressions decrease in rate as the temperature decreases. Thus, a minimal temperature of about 15 degrees is preferred.

The reactant ligand is present in a reaction mixture in an amount up to its solubility in the aqueous medium. A two phase system that includes insoluble reactant ligand can also be used, but normally is not so used. Normally used concentrations of the reactant ligand are about 0.1 micromolar (uM) to about 10 millimolar (mM), with that amount also being a function of the solubility of the reactant ligand in the solvent medium. Where the product is desired, per se, relatively higher concentrations are used as compared to lower concentrations where a reaction mechanism or reaction kinetics are to be studied.

An effective amount of the receptor molecule is also present. That effective amount is typically a catalytic amount; i.e., the receptor is used at a molar ratio to the reactant ligand of about 1:2 to about 1:10,000, with a molar ratio of about 1:10 to about 1:100 being preferred. The ratio of receptor molecule to reactant ligand typically depends upon the specific activity of the receptor molecule toward the reactant ligand and the purpose of the user in running the reaction. Thus, where the product is desired, a relatively higher concentration of receptor and higher receptor to reactant ligand ratio are used. Where the reaction mechanism or kinetics of the reaction are being studied, a lower concentration and ratio are typically used. A stoichiometric amount of receptor or less can also be used, but since the receptor is a catalytic molecule, use of even a stoichiometric amount can be wasteful. Thus, at least a catalytic amount of the receptor is utilized.

As discussed herein, exemplary receptors are secreted by hybridomas having ATCC accession numbers HB 9168, HB 9169, HB 9500, HB 9501, HB 9502, HB 9503, HB 9504, HB 9505, HB 9506, HB 9507, HB 9508, and HB 9509 and the reactant ligand molecules have a structure as described herein.

III. Preparation of Analog-Ligands and Ligands

The following sequences relate to the preparation of Compounds 1-11 that are shown in FIG. 2, as well as to Compounds 12-22. For ease of description, the preparation of Compounds (analog-ligands) 3, 4, 1 and 2, and Compounds (reactant ligands) 5, 6, 7, 8, 10, 11 and 9 are described in that order. The preparation of inhibitors to the catalytic cleavage of Compounds 1-4 and 12 is also described; i.e., Inhibitors 1i, 2i, 3i, 4i, and 12i respectively.

Diethyl 4-trifluoroacetamidobenzyl phosphonate (Compound A)

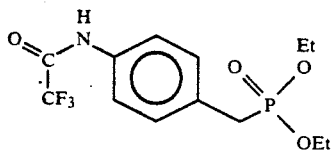

To a stirred solution of diethyl 4-aminobenzyl phosphonate (0.74 g, 3.04 mM) in 5 ml methylene chloride (freshly distilled over calcium hydride) is added (0.32 ml, 4 mM) pyridine. The mixture is cooled to 4 degrees C. and trifluoroacetic anhydride (0.5 ml, 3.54 mM) is added dropwise over a 5 minute period to the stirring solution. Stirring is continued for 15 minutes while the solution is allowed to warm to room temperature (about 23 degrees C.). Completion of the reaction is indicated by thin layer chromatography using a 1:1 mixture of methylene chloride and ethyl acetate as eluant ($R_f$ 0.2). solution is diluted with 50 ml of ethyl acetate. The organic solution is washed twice with successive 25 ml portions of 0.5 M HCl and is then dried over anhydrous magnesium sulfate. Evaporation provides a yellow oil that is purified by flash chromatography on silica gel using a 1:1 mixture of methylene chloride and ethyl acetate as eluant. The phosphonate (Compound A) (0.877 g, 85 percent yield) is obtained as a colorless crystalline material.

Proton NMR in CDCl$_3$ at 100 MHZ: delta 10.61 (broad singlet, 1H), 7.53 (doublet, J=8.22 Hz, 2H), 7.17 (double doublet, J=8.67 Hz and 2.5 Hz, 2H), 4.02 (P, J=7.18 Hz, 2(2H)), 3.10 (doublet, J=21.62, Hz, 2H) and 1.26 (triplet, J=7.05 Hz, 2(3H)). Ethyl chloro 4-trifluoroacetamidobenzyl phosphonate (Compound B)

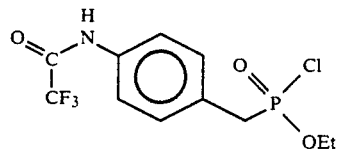

To a solution of the phosphonate (Compound A) (0.1 g, 0.29 mM) in 5 ml chloroform (freshly distilled over calcium hydride) is added phosphorus pentachloride (PCl$_5$) (0.070 g, 0.35 mM). The reaction is stirred at 50 degrees C. for 2 hours. Completion of the reaction is indicated by thin layer chromatography whereby an aliquot is removed and quenched in methanol and triethylamine. Chromatography is performed using a 1:1 mixture of methylene chloride and ethyl acetate as eluant ($R_f$ 0.3). The remaining PCl$_5$ is quenched by heating solid sodium bisulfite and bubbling it into the reaction mixture. Solvent evaporation yields a yellow oil which provides a white crystalline solid upon addition of 30 ml anhydrous diethyl ether. The precipitate is washed three times with successive 30 ml portions of diethyl ether to provide the chloro phosphonate (Compound B) (0.086 g, 89 percent yield). Compound B is used directly without further purification due to its hydroscopic nature.

Proton NMR in CDCl$_3$ at 100 MHz: delta 9.09 (broad singlet, NH), 7.55 (doublet, J=7.72 Hz, 2H), 7.28 (multiplet, 2H), 4.29 (P, J=7.12 Hz, 2H), 3.52 (doublet, J=20.5 Hz, 2H) and 1.39 (triplet, J=7.07 Hz, 3H).

2-Hydroxy-5-nitro-benzyl hexamethylenetetramine Hydrobromide (Compound C)

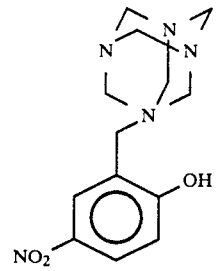

Hexamethylenetetramine (1.88 g, 8.1 mM) is dissolved in 20 ml of chloroform (freshly distilled over calcium hydride). 2-Hydroxy-5-nitrobenzylbromide (1.137 g, 8.1 mM) is added to the stirred solution. The slurry is refluxed overnight, which upon cooling provides a bright yellow precipitate. The precipitate is filtered and washed three times with successive 50 ml portions of cold chloroform to provide 3.010 g (100 percent yield) of the quaternary salt (Compound C) upon drying under vacuum. Compound C has a melting point of 181-184 degrees C.

Proton NMR in (CD3)2SO at 100 MHz: delta 8.06 (doublet, J=2.79 Hz, 1H), 7.96 (double doublet, J=8.92 and 2.74 Hz, 1H), 6.92 {doublet, J=8.87 Hz, 1H), 4.91 (broad singlet, 6H) and 3.84 (singlet, 2H).

2-Hydroxy-5-nitro benzylamine hydrochloride (Compound D)

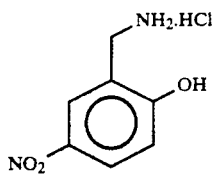

To 15 ml of ethanol is added (0.250 g, 0.67 mM) of Compound C and concentrated HCl (0.56 ml, 0.67 mM). The yellow slurry is refluxed for 2.5 hours until the solution is clear. Upon cooling, a white precipitate is formed (an ammonium bromide salt). The precipitate is filtered and the filtrate is concentrated to dryness to provide an off-white precipitate. The precipitate is stirred in acetone, and the slurry is filtered to provide 0.128 g (94 percent) of the amine (Compound D). Thin layer chromatography is performed with a 1.2 percent/5/1 mixture of ammonium hydroxide/methylene chloride/methanol as eluant ($R_f$ 0.2). The product provides a positive ninhydrin test. The melting point of the amine (Compound D) is 248–251 degrees C. (with decomposition).

Proton NMR in $(CD_3)_2SO$ at 100 MHz: delta 7.93 (doublet, J=3.10 Hz, 1H), 7.83 (double doublet, J=9.23 and 3.07 Hz), 6.14 (doublet, J=9.17 Hz, 1H) and 3.80 (singlet, 2H).

Hydroxy-5-nitrobenzamide, 6-methyl ester pyridine (Compound E)

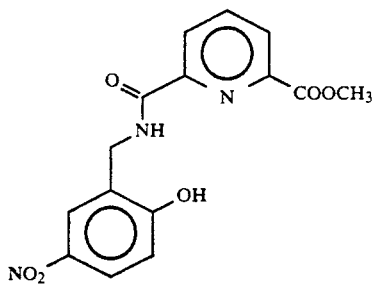

2-Hydroxy-5-nitro benzylamine hydrochloride (Compound D) (0.259 g, 1.27 mM) is added to a solution of dipicolinic acid monomethyl ester chloride (0.254 g, 1.27 mM) in methylene chloride (freshly distilled over calcium hydride) to provide a slurry which is stirred vigorously. Triethylamine (0.53 ml, 3.81 mM) is added dropwise to provide a yellow colored solution, which then turns orange upon complete addition of the triethylamine. Completion of the reaction is indicated by thin layer chromatography using a 39:1 mixture of methylene chloride and ethanol as eluant ($R_f$ 0.2). The solution is diluted with 50 ml ethyl acetate and is washed three times with successive 25 ml portions of 0.5 M HCl, and brine. After drying over anhydrous magnesium sulfate and evaporation of solvent, 0.375 g of product is obtained. This is subjected to flash chromatography on silica gel using a 19:1 mixture of methylene chloride and ethanol as eluant. The amide (Compound E) (0.310 g, 74 percent) was obtained as an opaque solid having a melting point of 236–238 degrees C.

Proton NMR in $(CD_3)_2SO$ at 100 MHz: delta 11.39 (broad singlet, NH), 9.15 (multiplet, 1H), 8.34–8.01 (multiplet, 4H), 6.98 (doublet, J=9.3, 1H), 4.52 (doublet, J=4.521, 2H) and 3.92 (singlet, 3H).

Preparation of Compound F

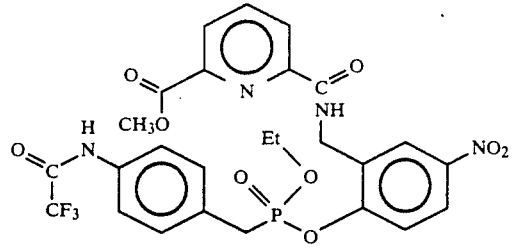

Compound E (0.19, 0.3 mM) is added to a solution of Compound B (0.099 g, 0.3 mM) in methylene chloride (distilled over calcium hydride). The slurry is stirred vigorously and triethylamine (0.66 ml, 9 mM) is added dropwise provide an oscillating yellow color. Upon complete addition of the triethylamine, the solution remains clear. The solution is stirred for an additional 15 minutes. Completion of the reaction is indicated by thin layer chromatography using a 20:1 mixture of methylene chloride and ethanol as eluant ($R_f$ 0.6). Dilution with a 30 ml portion of ethyl acetate followed by two washings with successive 30 ml portions of 0.5 M HCl, and brine, followed by drying over anhydrous magnesium sulfate and solvent evaporation yields a yellow oil. This product is further purified by flash chromatography silica gel using a 35:1 mixture of methylene chloride and ethanol as eluant. The nitrophosphonate (Compound F) (0.154 g, 82 percent yield) is obtained as a white foam.

Proton NMR in $CDCl_3$ at 100 MHz: delta 9.41 (broad singlet, NH), 8.51–7.93 (multiplet, 5H), 7.71 (doublet, J=8.20 Hz, 2H), 7.55 (doublet, J=8.89 Hz, 1H), 7.35 (double doublet, J=8.62 and 2.51 Hz, 2H), 4.45 (doublet, J=6.54 Hz, 2H), 4.24 (multiplet, 2H), 4.01 (singlet, 3H), 3.46 (doublet, J=20.8 Hz, 2H) and 1.27 (triplet, J=6.94 Hz, 3H).

Preparation of Compound G

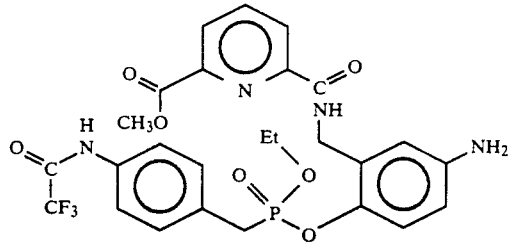

To a stirred solution of Compound F (0.061 g, 97 mM) in ethanol is added concentrated hydrochloric acid (200 ml, 6.6 mM). Stirring is stopped and 0.032 g palladium on carbon is added. The reaction mixture is placed under a hydrogen atmosphere and is stirred vigorously for 1 hour. Completion of the reaction is indicated by thin layer chromatography using a 20:1 mixture of methylene chloride and ethanol as eluant ($R_f$ 0.4). The product provides a positive ninhydrin test. Dilution with 25 ml ethyl acetate is followed by filtration through Celite. The filter cake is rinsed twice with successive 25 ml portions of ethyl acetate. The organic layer is washed with an aqueous solution of 5 percent sodium bisulfite until it is basic, followed by washing with two successive 25 ml portions of brine, drying over anhydrous magnesium sulfate and evaporation to provide the amine (Compound G) as a clear oil (0.038 g, 69 percent yield) having a purity suitable for the next step.

Proton NMR in CDCl₃ at 100 mHz: delta 9.05 (broad singlet, NH), 8.42-7.92 (multiplet, 3H), 7.71 (doublet, J=8.33 Hz, 2H), 7.35 (doublet, J-8.84 Hz, 1H), 7.15 (double doublet, J=8.37 and 2.31 Hz, 2H), 6.75 (doublet, J=3.22 Hz, 1H), 1.51 (double doublet, J=8.80 and 3.91 Hz, 1H), 4.92 (doublet, J=6.85 Hz, 2H), 4.10 (multiplet, 2H), 4.05 (singlet, 3H), 3.39 (doublet, J=21.38 Hz, 2H) and 1.22 (triplet, J=6.95 Hz, 3H).

Preparation of Compound 3

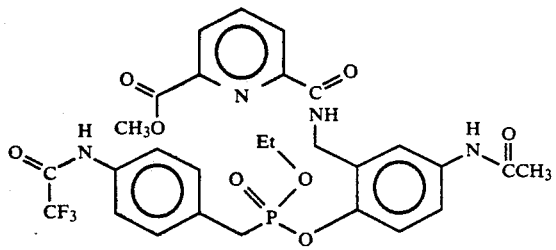

A sample of the amine (Compound G) (0.063 g, 0.106 mM) is dissolved in 8 ml methylene chloride (distilled over calcium hydride). Acetic anhydride (0.150 ml, 1.35 mM) is added followed by triethylamine (0.075 ml, 1.02 mM). The reaction is followed by thin layer chromatography until completion using a 9:1 mixture of methylene chloride and methanol as eluant (R_f 0.2). Dilution with 35 ml ethyl acetate is followed by three successive washings with 20 ml portions of 0.5 M HCl, 10 percent sodium bicarbonate and brine. Evaporation of the solvent is followed by flash chromatography on silica gel using a 10:1 mixture of methylene chloride and methanol as eluant to provide compound 3 (0.045 g, 67 percent yield) Compound 3 is shown to be analytically pure by HPLC on an analytical RP-C18 column (Vydac 218TP54) using 30-90 percent acetonitrile in water at a flow rate of 1 ml per minute for 20 minutes to provide a single peak at 57 percent.

Proton NMR in CDCl₃ at 100 MHz: delta 9.61 (broad singlet, NH), 8.41-8.22 (multiplet, 4H), 8.21-7.59 (multiplet, 3H), 7.58-7.14 (multiplet, 4H), 4.22 (multiplet, 4H), 4.05 (singlet, 3H), 3.40 (doublet, J=21.25 Hz, 2H), 2.12 (singlet, 3H) and 1.23 (triplet, J=6.93 Hz, 3H).

Preparation of Compound 4

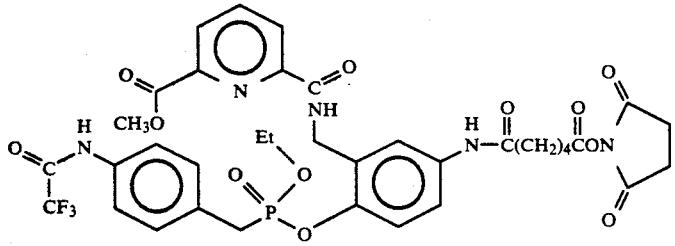

A stirred solution of the amine (Compound G) (0.035 g, 59 mM) in tetrahydrofuran (distilled over sodium in the presence of benzophenone) is treated under nitrogen via syringe with 0.140 ml of 0.5 M solution of To this solution is added triethylamine (0.025 ml, 180 mM). The reaction is followed until completion by thin layer chromatography using a 5:1 mixture of methylene chloride and ethanol as eluant (R_f 0.6). Dilution with a 25 ml portion of ethyl acetate followed by two washings with successive 25 ml portions of 0.5 M HCl, and brine, followed by drying over anhydrous magnesium sulfate and solvent evaporation yields a yellow oil. This product is further purified by flash chromatography on silica gel using a 10:1 mixture of methylene chloride and ethanol as eluant. The nitrophosphonate (Compound 4) (0.036, 82 percent yield) is obtained as a white foam. This product is shown to be analytically pure by HPLC using the column described above and eluting with 30-90 percent acetonitrile in water at a flow rate of 1 ml per minute for 25 minutes) to provide one peak.

Proton NMR in CDCl₃ at 100 MHz: delta 9.29 (broad singlet, NH), 8.43-8.25 (multiplet, 4H), 8.24-7.67 (multiplet, 3H), 7.66-7.10 (multiplet, 3H), 4.24 (multiplet, 4H), 4.05 (singlet, 3H), 3.40 (doublet, J=21.30 Hz, 2H), 2.84 (singlet, 4H), 2.65 (multiplet, 2H), 2.38 (multiplet, 2H), 2.38 (multiplet, 2H), 1.79 (multiplet, 4H) and 1.26 (triplet, J=6.91 Hz, 3H).

Preparation of Inhibitor 3i

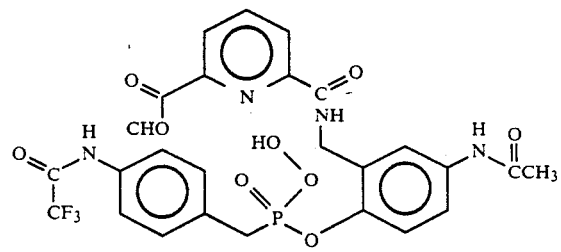

The phosphonate (Compound 3) (0.065 g, 0.1 mM) is dissolved in 2.5 ml of acetonitrile (distilled over calcium hydride). Sodium iodide (0.306 g, 2 mM) is added to the solution followed by trimethyl silylchloride (0.26 ml, 2 mM) producing an orange colored solution. The reaction is heated at 60 degrees C. After 12 hours of heating and stirring, one major peak was observed at 42 percent by HPLC using the column described above and eluting with 30-90 percent acetonitrile in water at a flow rate of 1 ml per minute for 20 minutes. The solution is allowed to cool to room temperature, and then is diluted with 10 ml of a 50:50 mixture of ethyl acetate and n-butanol. The organic layer is stirred with a solution of brine, while solid, sodium bisulfite is added until the orange color faded. The layers are separated and the aqueous phase is extracted with two consecutive 10 ml portions of ethyl acetate and n-butanol. The combined organic layers were dried over sodium sulfate and buffered using sodium acetate (0.030 g). The solvent is removed by rotary evaporation giving (0.088 g, 145 percent yield) of a white powder. This product is then dissolved in 5 ml of water and cooled to zero degrees C. The resulting solution is acidified with 6 M HCl to pH 2. Lyophilization of the acidified solution yielded 0.085 grams of Inhibitor 3i. This was then subjected to a C₁₈

Waters reverse phase Sep-Pack, (Waters Associates, Millipore Corp., Milford, Mass.), eluting with 10 percent acetonitrile in water, and fractions 4, 5 and 6 were collected. The fractions were combined and re-checked by HPLC, showing one peak at 42 percent. The solution was lyophilized.

Preparation of Compound 4i (used for immunizations)

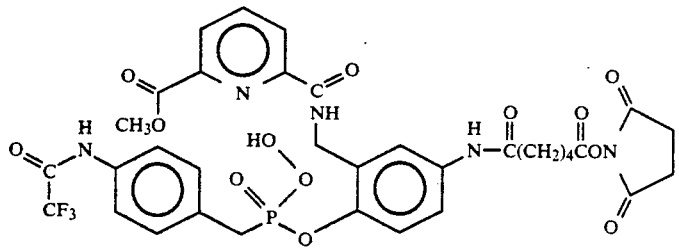

A 23.5 mg sample of Compound 4 is dissolved in 2 ml acetonitrile (distilled over calcium hydride). This is then subjected to the procedure used to deblock Inhibitor 3i. The sample is analytically pure by HPLC using the column described above and eluting with 30–90 percent acetonitrile in water at a flow rate of 1 ml per minute for 30 minutes) to provide one major peak 4i at 49 percent. Buffering the organic phase with sodium acetate followed by solvent removal provided Compound 4i (0.036 g, 162 percent yield). Though this product is still contaminated with inorganic salts, the sample is suitable for coupling to protein carriers (including BSA and KLH). Compound 4i is prone to hydrolysis (NHS group) and should be stored at zero degrees C. in a dessicator. Purity of Compound 4i could be checked by treatment with diazomethane. The reaction is followed by thin layer chromatography using a 10:1 mixture of methylene chloride and ethanol as eluant ($R_f$ 0.4) and showed one spot which co-spotted with Compound 4. $P^{31}$ NMR is DMSO at 100 MHz: delta 22.2 (singlet).

Preparation of Compound H

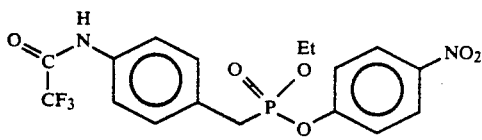

The phosphonyl chloride (Compound B) (0.726 g, 2.2 mM) is dissolved in dry chloroform (distilled over calcium hydride). To this is added p-nitrophenol (0.305 g, 2.2 mM) and triethylamine (0.32 ml, 2.5 mM). The reaction is stirred for 10 minutes and completion is indicated by thin layer chromatography in a 1:1 mixture of methylene chloride and ethanol as eluant ($R_f$ 0.8). Dilution with a 50 ml portion of ethyl acetate followed by three washings with successive 50 ml portions of 0.5 M HCl, saturated sodium bicarbonate and brine, drying and evaporation provided Compound H. Further purification by flash chromatography on silica gel was performed using a 2:1 mixture of methylene chloride and ethanol as eluant to provide the phosphonate (Compound H) (0.626 g, 66 percent yield).

Proton NMR in CDC13 at 100 MHz: delta 8.79 (broad singlet, NH), 8.19 (doublet, J=9.44 Hz, 2H), 7.54 (doublet, J=8.21 Hz, 2H), 7.25 (double doublet, J=8.57, and 2.62 Hz, 2H), 7.20 (doublet, J=9.13 Hz, 2H), 4.17 (p, J=7.15 Hz, 2H), 3.35 (doublet, J=21.77 Hz, 2H) and 1.29 (triplet, J=6.94 Hz, 3H).

Preparation of Compound I

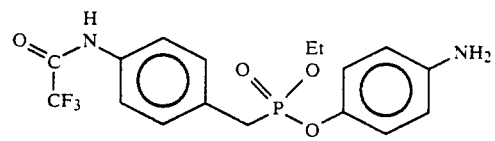

A sample of Compound H (0.250 g, 0.63 mM) is reduced in a similar procedure as described for the reduction of Compound F. The amine (Compound I) is obtained as a clear foam (0.130 g, 51 percent yield). Thin layer chromatography was performed using a 1:1 mixture of methylene chloride and ethanol as eluant ($R_f$ 0.3). The product provides a positive ninhydrin test.

Proton NMR in CDCl$_3$ at 100 MHz: delta 8.51 (broad singlet, NH), 7.63 (doublet, J=8.19 Hz, 2H), 7.31 (double doublet, J=8.61 and 2.51 Hz, 2H), 7.24 (doublet, J=8.91 Hz, 2H), 6.61 (doublet, J=8.06 Hz, 2H), 4.18 (p, J=7.18 2H), 3.39 (doublet, J=21.55 Hz, 2H) and 1.24 (triplet, J=7.18 Hz, 3H).

Preparation of Compound 1

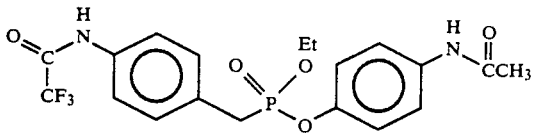

To a solution of methylene chloride (freshly distilled over calcium hydride) is added (0.030 g, 0.075 ml) of Compound I. The acylation of Compound I is performed in a similar manner already described for the acylation of Compound G. Compound 1 is obtained as a foam (0.024 g, 73 percent yield). Thin layer chromatography was performed using a 4:1 mixture of methylene chloride and ethanol as eluant ($R_f$ 0.3).

Proton NMR in CDC1$_3$ at 100 MHz: delta 9.57 (broad singlet, NH), 8.28 (broad singlet, NH), 7.50 (doublet, J=8.21 Hz, 2H), 7.39 (doublet, J=8.34 Hz, 2H), 7.18 (double doublet, J=8.31 and 2.59 Hz, 2H), 4.13 (p, J=7.3 Hz, 2H, 3.26 (doublet, J=21.73 Hz, 2H), 2.07 (singlet, 3H) and 1.24 (triplet, J=7.10 Hz, 3H).

Preparation of Compound 2

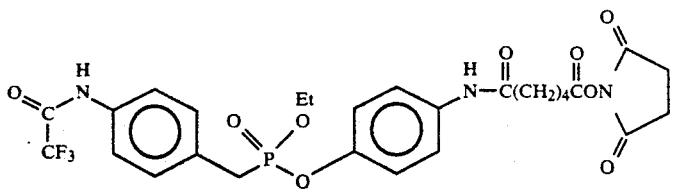

Compound I (0.168 g, 0.42 mM) is reacted in an analogous procedure already described in the synthesis of Compound 4. Compound 2 is obtained as a clear glass (0.188 g, 71 percent yield).

Proton NMR in CDC13 at 100 MHz: delta 9.35 (broad singlet, NH), 8.39 (broad singlet, NH), 7.53 (doublet, J=8.15 Hz, 2H), 7.41 (doublet, J=8.29 Hz, 2H), 7.19 (double doublet, J=8.30 and 2.57 Hz, 2H), 4.15 (p, J=7.21 Hz, 2H), 3.25 (doublet, J=21.67 Hz, 2H), 2.85 (singlet, 4H), 2.61 (multiplet, 2H), 2.33 (multiplet, 2H), 1.79 (multiplet, 4H) and 1.23 (triplet, J=7.23 Hz, 3H).

Preparation of Inhibitor 1i

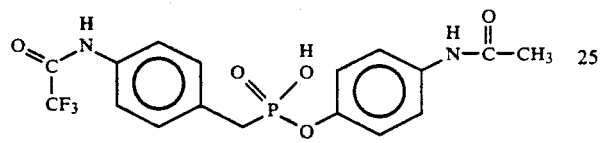

The phosphonate (Compound 1) (0.030 g, 68 mM) is dissolved in 3 ml acetonitrile (freshly distilled over calcium hydride). Trimethyl silylbromide (0.1 ml, 76 mM) is added slowly and the reaction is heated to 50 degrees C. for 45 minutes. The solution is allowed to cool to room temperature. Completion is indicated by reverse phase thin layer chromatography using a 3:7 mixture of ispropanol and water ($R_f$ 0.8). Dilution with 30 ml of a 1:1 mixture of ethyl acetate and n-butanol, and two washings with successive 30 ml portions of 0.5 M HCl, brine followed by drying and evaporation provided Inhibitor 1i (0.023 g, 83 percent yield). This was further purified according to the method described for Inhibitor 3i.

Proton NMR in (CD3)2SO at 100 MHz: delta 9.15 (broad singlet, NH), 8.17 (broad singlet, NH), 7.71–6.95 (multiplet, 8H), 2.23 (doublet, J=21.65 Hz, 2H) and 2.09 (singlet, 3H).

Preparation of Compound 2i (used for immunizations)

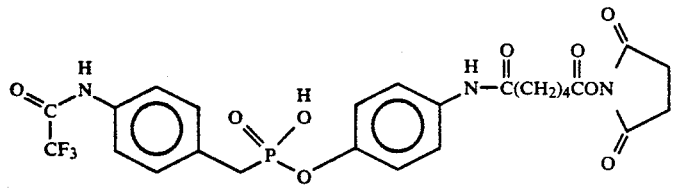

A 20 mg sample of Compound 2 was dissolved in 2 ml acetonitrile (freshly distilled over calcium hydride). This is then treated with trimethyl silylbromide (0.05 ml, 31 mM) and is heated to 50 degrees C. for 2 hours. Completion of the reaction is indicated by thin layer chromatography using a 2:1 mixture of methylene chloride and ethanol as eluant ($R_f$ 0.7). The solvent is removed by rotary evaporation and the residue is dissolved in 20 ml of a 1:1 mixture of ethyl acetate and n-butanol. The organic layer is washed twice with successive 25 ml portions of water then brine. The organic layer is concentrated to provide a white powder, Compound 2i (0.017 g, 87 percent yield). This is found suitable for protein coupling and no further purification is needed.

Preparation of Compound 5

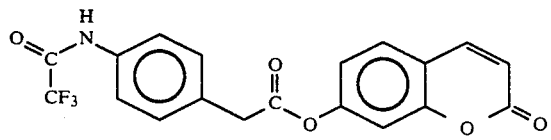

Trifluoracetic anhydride (2.8ml) was added to a solution of 4-aminophenyl acetic acid (1.5 g) and sodium carbonate (1.5 g) in 10 percent aqueous acetonitrile at −10 degrees C. The solution was acidified with 6 Normal HCl (0.2 ml) and was concentrated in vacuo. Filtration through silica with a 9:1 mixture of dichloromethane and methanol provided 1.4 grams (57 percent yield by weight) of p-trifluoroacetamidophenyl acetic acid. Thin layer chromatography on silica gel using a 5:1 mixture of chloroform and methanol as eluant provided an $R_f$ value of 0.35.

Proton NMR (in CDCl3) delta 3.15 (singlet, 2H), delta 7.02 (double doublet, 4H), delta 10.4 (broad singlet, NH).

The foregoing acid (0.6 g) was dissolved in thionyl chloride and the solution was heated at 40 degrees C. for 2 hours. The thionyl chloride was removed in vacuo, and the residue was dissolved in dichloromethane (5 ml) and added to a solution of 7-hydroxycoumarin (0.40 g) and triethylamine (0.70 ml) in dichloromethane (5 ml). After 10 minutes the solution was diluted with ethyl acetate (50 ml) and washed with 5 percent HCl, then with brine. The organic solution was dried and concentrated. Silica gel chromatography using a 15:1 mixture of dichloromethane and ethyl acetate as eluant provided 0.83 g (81 percent yield by weight) of Compound 5 as a white solid. Thin layer chromatography with silica gel using a 9:1 mixture of dichloromethane and ethyl acetate as eluant provided an $R_f$ value of 0.78.

Proton NMR (in CD3CN): delta 3.95 (singlet, 2H), delta 6.40 (doublet, 1H), delta 7.0–7.7 (multiplet, 7H), delta 7.85 (doublet, 1H), delta 9.2 (broad singlet, NH).

Preparation of Compound 6

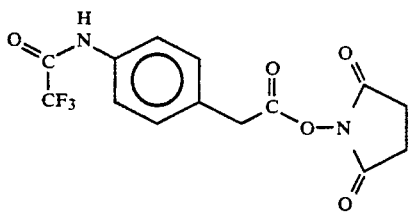

p-Trifluoroacetamidophenylacetyl chloride was treated with N-hydroxysuccinimide and triethylamine in dichloromethane to provide Compound 6 as a white solid after purification in the manner described above with reference to Compound 5. Thin layer chromatography with silica gel using a 5:1 mixture of chloroform and methanol as eluant provided an $R_f$ value of 0.35.

Proton NMR (in CDCl$_3$): delta 3.15 (singlet, 2H), delta 7.02 (doublet doublet, 4H) and delta 10.4 (broad singlet, NH).

Preparation of Compound 7

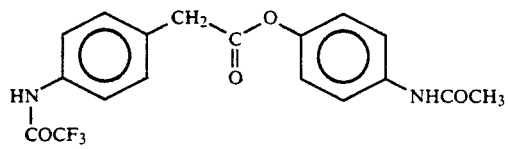

A mixture of 4-trifluoroacetamidophenylacetic acid and thionyl chloride was heated for 2 hours at 40 degrees C. The volatile components were removed in vacuo. The residue was dissolved in dichloromethane. 4-Acetamidophenol (1 equiv.) was added, followed by triethylamine. The product (Compound 7) was purified and isolated by the extraction and chromatographic procedures described above with reference to the foregoing compounds.

Preparation of Compound 8

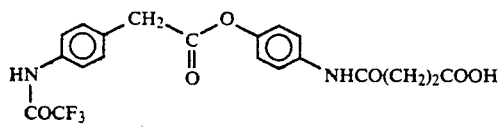

4-Trifluoroacetamidophenylacetyl chloride was treated with p-nitrophenol and triethylamine in dichloromethane. The p-nitrophenyl ester was obtained by extraction and chromatography on silica gel.

The p-nitrophenyl ester was stirred in methanol and formic acid (50:1) over 10 percent palladium on charcoal. Hydrogen gas was bubbled into the mixture for 2 hours The mixture was then diluted with ethyl acetate and filtered The filtrate was washed with 5 percent aqueous sodium bicarbonate and brine, filtered and concentrated to provide the p-aminophenyl ester This ester was reacted with succinic anhydride and triethylamine in dichloromethane to obtain Compound 8.

Preparation of Compound 10

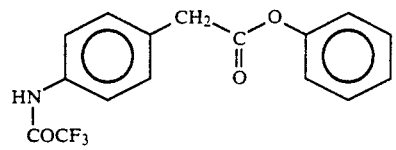

4-Trifluoroacetamidophenylacetyl chloride and phenol were dissolved in dichloromethane and treated with triethylamine. The product (Compound 10) was separated by extraction and chromatography on silica gel using the procedures described above.

Preparation of Compound 11

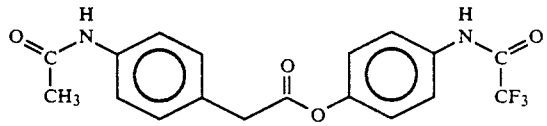

4-Acetamidophenylacetic acid was prepared from 4-aminophenylacetic acid and acetic anhydride in aqueous acetonitrile and sodium bicarbonate.

A 4-trifluoroacetamidophenol was prepared in two steps from 4-nitrophenol by reduction with H2/palladium on charcoal in methanolic HCl, and acetylation with acetic anhydride in aqueous acetonitrile.

A mixture of this acid and 4-trifluoroacetamido phenol in dichloromethane was treated with bis(2-oxo-3-oxazolidinyl) phosphinic chloride (BOP-Cl, a commercial reagent available from Aldrich Chemical Co., Milwaukee, Wis.) and triethylamine for 1.5 hours at room temperature. Compound 11 was obtained according to the previously described separation procedures.

Preparation of Compound 9

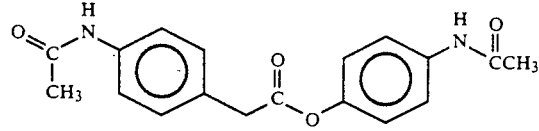

By a similar procedure a mixture of this acid and 4-acetamidophenol were combined with BOP-Cl and triethylamine in dichloromethane. Analogous separation according to the previously described procedures provided the ester (Compound 9). Determination of pKa and stability constants K:

All determinations of pKa and stability constants (K) are performed according to the method of Martell. This method consisted of potentiometric titration of the particular compound (at a concentration of about 1.4 mM) in the absence of and in the presence of the metal ion being investigated. The ionic strength was maintained constant using 0.1 M NaClO$_4$ as a supporting electrolyte. All measurements were carried out under nitrogen at 25 degrees C. plus or minus 0.01 degrees C.

Preparation of Compound J

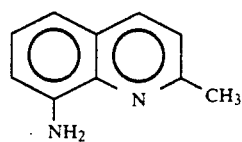

2-Methyl-8-nitro-quinaldine (0.5 g; 2.66×10⁻³ moles) is placed in a 25 ml round bottom flask along with 15 ml of methanol and then 0.081 ml of concentrated HCl (1 equivalent). The mixture is stirred for 5 minutes and 0.250 g of palladium on carbon are added. The resulting admixture is placed under an atmosphere of hydrogen gas and the nitro group reduced. After stirring for 25 minutes, the reaction mixture is checked for completion by thin layer chromatograpy on silica (TLC) using hexane/ethyl acetate (1/1) as solvent. No starting material is observed The product has an $R_f$ value of 0.85 and stains black with ninhydrin.

The reduced reaction mixture is diluted with 50 ml of ethyl acetate (EtoAc), filtered through a celite bed, and concentrated in vacuo. The resulting oil is redissolved in 50 ml of EtoAc, and extracted with saturated aqueous sodium bicarbonate and then with saturated sodium chloride, and dried over sodium sulfate. Upon removal of the solvent in vacuo, 0.353 g of a yellow solid are obtained (84% yield).

Proton NMR in CDCl₃ at 100 MHz (relative to TMS as internal standard): 7.95 (doublet, J=7.92 Hz, 1H), 7.4–6.8 (multiplet, 4H), 5.0 (broad singlet, 2H), 2.75 (singlet, 3H).

Preparation of Compound 12

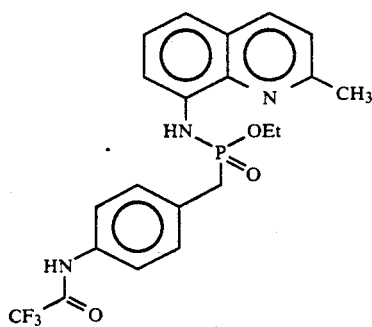

Compound J (0.037 g; 2.34×10⁻⁴ moles) is placed in a 25 ml round bottom flask under a nitrogen atmosphere. Tetrahydrofuran (THF; 5 ml) is added to dissolve Compound J, and the resulting solution is cooled to −78 degrees C. A solution of butyl lithium (110 ml, 2.5 M in hexanes) is added slowly over a 5 minute time period to obtain a purple, black solution. After stirring for an additional 5 minutes, Compound B is added and the resulting admixture is allowed to warm to room temperature; the solution color becomes light green. TLC on silica with EtoAc/CH₂Cl₂ (1/1) as solvent shows the product to have an $R_f$ value of 0.4.

The solvent is removed in vacuo and the resulting material is redissolved in 20 ml of EtoAc, washed in 0.5 M HCl and saturated aqueous sodium chloride, and then dried over sodium sulfate. The solvent is removed in vacuo, and 0.042 g (40% yield) of Compound 12 are obtained after flash chromatography.

Proton NMR in CDCl₃ at 100 MHz (relative to TMS as internal standard): 10.4 (broad singlet, 1H) 8.0 (doublet, J=7.7 Hz, 1H), 7.7 (doublet, J=7.9 Hz, 1H), 7.4–6.8 (multiplet, 7H), 4.2 (p, J=5.2 Hz), 3.35 (doublet, J=20.1 Hz, 2H), 2.6 (singlet, 3H), 1.3 (triplet, J=6.2H).

Preparation of Compound K

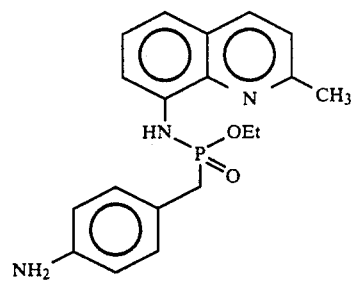

Compound 12 (0.010 g, 2.22×10⁻⁵ moles) is placed into a 5 ml round bottom flask to which are added 1.5 ml of methanol and 8 mg of solid sodium carbonate (8.88×10⁻⁵ moles), followed by 200 ml of water. The reaction was followed by TLC on silica using EtoAc/CH₂Cl₂ (1/1) as solvent; the product having an $R_f$ value of 0.35. The reaction is stopped after 12 hours at a temperature of 35 degrees C.

The reaction mixture is diluted with EtoAc, marked with saturated sodium chloride, and dried over sodium sulfate. The solvent is thereafter removed in vacuo to obtain 6.5 mg of Compound K (83% yield).

Proton NMR in CDCl₃ at 100 MHz (relative to TMS as internal standard): 8 (doublet, J=7.1 Hz, 1H), 7.7–6.0 (multiplet, 9H), 6.6 (doublet, J=7.1 Hz, 1H), 4.2 (multiplet, 2H), 3.3 (doublet, J=20.1 Hz, 2H), 2.7 (singlet, 3H, 1.3 (triplet, J=6.6Hz, 3H)

10 Preparation of Compound L

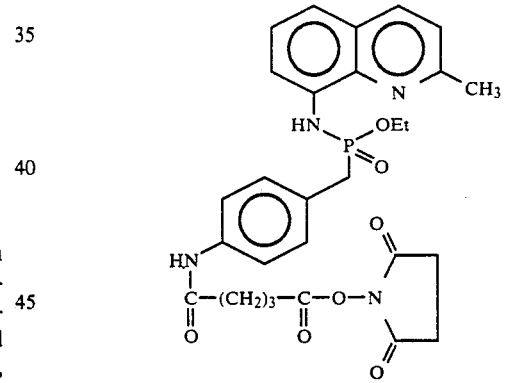

Compound K (0.0065 g, 1.84×10³¹ ⁵ moles) is placed in a 5 ml round bottom flask to which are added 2 ml of CH₂, 16.4 mg (4×10⁻⁵ moles) of succinimidyl glutaryl chloride (prepared in a manner analogous to that for the adipoyl derivative discussed hereinafter) and then triethylamine (0.003 ml, 4×10⁻⁵ moles). An immediate color burst is observed. The reaction is followed by TLC on silica using EtoAc/CH₂Cl₂ (1/1) as solvent, wherein the product has an $R_f$ value of 0.3. The reaction mixture is stirred for a total of 30 minutes, and then diluted with EtoAC, washed with 0.5 M HCl and with saturated sodium chloride, and then dried over sodium sulfate. Following solvent removal in vacuo, flash chromatography yields 3.5 mg of Compound L (34% yield).

Proton MNR in CDCl₃ at 100 MHz (relative to TMS as internal standard): 8.0 (doublet, J=7.1 Hz, 1H), 7.8–7.0 (multiplet, 10H), 4.2 (multiplet, 2H), 3.3 (doublet, J=20.2 Hz, 2H), 2.9 (singlet, 4H), 2.7 (singlet, 3H), 2.6–1.9 (multiplet, 6H), 1.3 (triplet, J=6.5 Hz).

Preparation of Compound 13

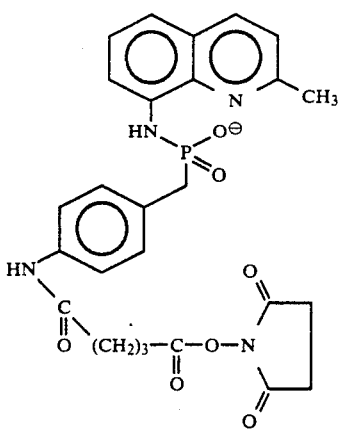

Compound L (0.012 g) is added to a dry NMR tube under nitrogen gas, followed by 1 ml of dry CDCl₃. Two 25 ml portions of trimethylsilylbromide (TMSBr) are added to the tube, and the tube is spun, and thereafter placed in a water bath at 38 degrees C. for a one hour time period. Cleavage of the ethyl ester of the phosphonamidate is monitored by NMR spectral data.

After ethyl ester cleavage is complete, the contents of the NMR tube are placed into a dry 10 ml round bottom flask under a nitrogen atmosphere. The solvent is removed in vacuo using a vacuum pump. The resulting solid is washed with mixed hexanes and again dried using a vacuum pump.

Solid sodium acetate (0.058 mg) is admixed with the above washed and dried solid, followed by 2 ml of an acetonitrile solution containing 10 ml of methanol. The resulting admixture is stirred with substantially everything present dissolving, but a small amount of a white solid remaining undissolved. This solution is frozen and lyophilized to provide a yellow, impure solid (38 mg).

Purity of Compound 13 is assayed by HPLC after dissolution in dimethyl formamide using a reverse phase C-18 column with the following gradient over 15 minutes:

| % A | % B |
|---|---|
| 25 | 75 |
| 70 | 30 |

A = acetonitrile
B = water-0.1% trifluoroacetic acid

One major peak is observed at 3.8 minutes. The material giving rise to that peak is stable at zero degrees C. over 5 days. Compound 13 is coupled to a carrier and used for immunizations with no further purification.

Preparation of Compound 12i

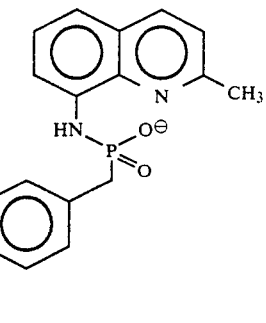

Compound 12 (15 mg, $3.3 \times 10^{-5}$ moles) is added to a dry NMR tube along with about 1 ml of CDCl₃. The solution is vortexed and two 35 ml portions of TMSBr are added. The resulting solution is vortexed further and then heated in a water bath for a period of 1 hour at 38 degrees C. Reaction progress is again monitored using NMR.

Upon completion of the reaction, the solution is removed from the tube, placed into a 10 ml round bottom flask and pumped dry with a vacuum pump to provide an orange solid. The solid is washed twice with 10 ml pontions of hexane and again pumped dry.

Solid sodium acetate trihydrate (45 mg) is admixed with the orange solid and 2 ml of acetonitrile containing 50 ul of methanol are added. The orange solid thereby provides a yellow solution.

Purity is again assayed using HPLC and a reverse phase C-18 column with the following gradient over 15 minutes:

| % A | % B |
|---|---|
| 25 | 75 |
| 90 | 10 |

A = acetonitrile
B = water-0.1% trifluonoacetic acid

The desired product, Compound 12i, elutes from the column at 5.80 minutes as one major peak. This material is stable at pH values of 3.5-7.3 for at least 11 days at room temperature.

Treatment of Compound 12i with diazomethane in methanol provides the corresponding methyl ester as further proof of the product's identity.

Proton NMR in CD₃CN at 100 MHz of Compound 12i obtained by preparative HPLC (relative to TMS as internal standard): 9.0 (broad singlet, 1H), 8.3 (doublet, J=7.3 Hz, 1H), 7.8-6.8 (multiplet, 9H), 3.3 (doublet J=21.0 Hz, 2H).

General Procedure for Preparing Substrate Ligand Esters

A suspension of 4-acetamidophenylacetic acid (5 m moles) BOP-Cl [5 m moles], triethylamine (10 m moles) and a hydroxy compound (5.2 m moles) in dichloromethane (10 ml) is stirred at room temperature (20–25 degrees C.) for one hour. The $R_f$ values were as follows using silica for the solid phase:

| Compound | $R_f$ | Solvent |
|---|---|---|
| 16 | 0.45 | CH₂Cl₂/EtoH (20/1) |
| 17 | 0.8 | CH₂Cl₂/EtoAc (1/1) |
| 22 | 0.7 | CH₂Cl₂EtoAc (1/1) |

-continued

| Compound | $R_f$ | Solvent |
|---|---|---|
| 21 | 0.5 | CH₂/Cl₂EtoAc (1/1) |

After treatment with water (10 ml, made basic with sodium bicarbonate), the organic layer is decanted and dried over sodium sulfate Removal of the solvent provides a residue, which, after flash chromatography using the above TLC solvent, provides the ester reactant ligant substrates as follows:

Compound 16

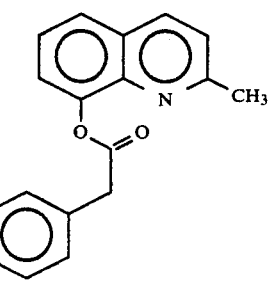

Yield=49%. Proton NMR in CDCl₃ at 100 MHz (relative to TMS as internal standard): 8.0 (broad doublet, J=7.2 Hz, 1H), 7.7-7.1 (multiplet 9H), 4.05 (singlet, 2H), 2.75 (singlet, 3H), 2.1 (singlet, 3H).

Compound 17

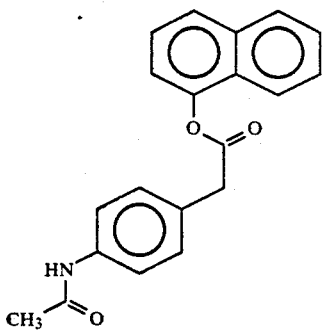

Yield=62%. Proton NMR in CDCl₃ at 100 MHz (relative to TMS as internal standard): 7.8-7.0 (multiplet 12H), 3.05 (singlet, 2H), 2.0 (singlet, 3H).

Compound 21

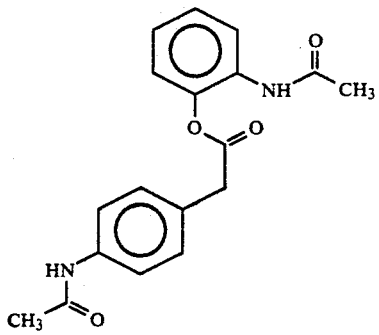

Yield=13%. Proton NMR in dimethyl sulfoxide —d₆ at 100 MHz (with TMS as internal standard): 7.6 (multiplet, 2H), 7.3 (multiplet, 2H), 6.9 (multiplet, 4H), 3.4 (singlet, 2H), 1.9 (singlet, 3H), 1.8 (singlet, 3H).

Compound 22

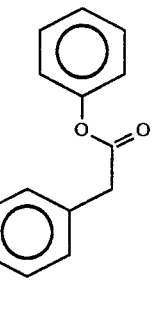

Yield=58%. Proton NMR in CDCl₃ at 100 MHz (relative to TMS as internal standard): 7.6-6.95 (multiplet 9H), 3.8 (singlet, 2H), 2.1 (singlet, 3H).

Compound 20

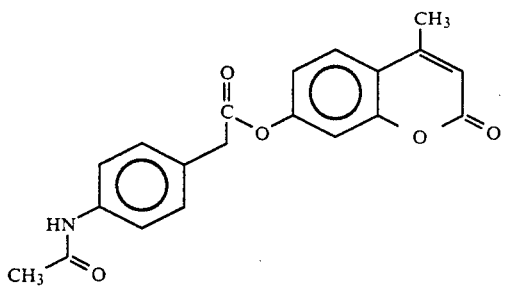

Compound 20 is prepared similarly to Compound 5.

Preparation of Compound 18

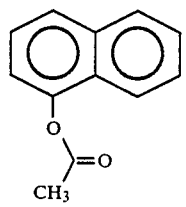

Alpha-naphthol (0.3515 g; 2.44×10⁻³ moles) is dissolved in 5 ml CH₂C₂, and the resulting solution is cooled to 0 degrees C. Acetyl chloride (0.26 ml; 3.66×10⁻³ moles) is added with stirring followed by a slow, dropwise addition of triethylamine (1.02 ml; 7.32×10⁻³ moles). A large amount of a precipitate is quickly formed that stops the stirring. An additional 5 ml of CH₂Cl₂ are added, and the reaction mixture is permitted to warm to room temperature.

Thin layer chromatography on silica using hexane/CH₂Cl₂ (1/1) as solvent, begun 5 minutes after the last addition of CH₂Cl₂, indicates that no starting material is present.

Ethyl acetate is added to the reaction mixture and the resulting admixture is extracted with aqueous sodium bicarbonate, 0.5 M HCl and then with saturated aqueous sodium chloride. The organic layer is thereafter dried over sodium sulfate. Following purification by column chromatography, 63 mg of a clear liquid are obtained; yield=42%.

Proton NMR in CDCl₃ at 100 MHz (relative to TMS as an internal standard): 8.0–7.2 (multiplet, 7H), 2.45 (singlet, 3H).

Preparation of Compound 19

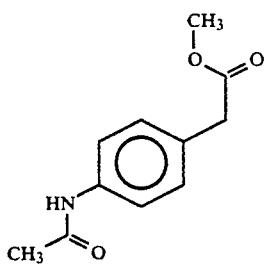

4-N-Acetylphenylacetic acid (0.00030 g; 1.55×10⁻⁴ moles) is dissolved in 5 ml of methanol. A solution of diazomethane in diethyl ether is added dropwise until the admixed solution remains yellow after such addition Cationic exchange resin beads in H⁺ form are admixed with the reaction solution until the solution is colorless.

The solvent is removed in vacuo to provide a white solid that weighs 0.032 g (100% yield). TLC on silica using CH₂Cl₂/EtoAc (1/1) as solvent indicates a clean reaction with no remaining starting material.

Proton MNR in CDCl₃ at 100 MHz (relative to TMS as internal standard): 7.2 (doublet, J=7.7 Hz, 2H), 6.8 (doublet, J=7.8 Hz, 2H), 3.95 (S, 3H), 3.2 (S, 2H).

General Procedure for Preparing
Substrate Ligand Amides

A stirred dichloromethane solution (20 ml) of the carboxylic acid (10 m moles), triethylamine (20 m moles) and amine (10 m moles) is cooled to 10 degrees C., and BOP-Cl (10 m moles) is added. Dissolution typically occurs within 30 minutues at 25 degrees C. The reaction is stirred at room temperature for a time period of 1 hour. The progress of the reaction is monitored by TLC on silica using EtoAc/CH₂Cl₂ as solvent. Compound 14 exhibits an $R_f$ value of 0.6 under these conditions.

Water (20 ml) and 4 M HCl are added to the reaction mixture to produce a pH value of 1–1.5. The precipitated amide is filtered off. The remaining organic layer is washed with a solution of sodium bicarbonate, and then evaporated to provide more of the amide product. Flash chromatography performed on silica with the TLC solvent provides the purified product.

Compound 14

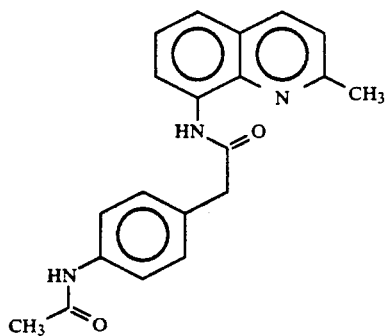

Yield=51%. Proton NMR in CDCl₃ at 100 MHz (relative to TMS as an internal standard): 10.0 (broad singlet, 1H), 8.7 (multiplet, 1 H), 8.0 (multiplet, 1H), 7.6–7.1 (multiplet, 8H), 3.95 (singlet, 2H), 2.6 (singlet, 3H), 2.2 (singlet, 3H).

Similarly prepared is Compound 15

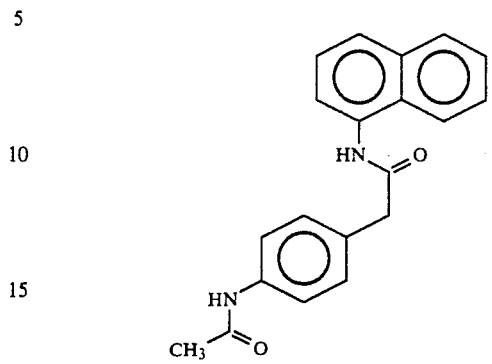

Preparation of Succinimidyl Adipoyl Chloride (Coupling Agent)

A solution of adipic acid monomethyl ester (5.4 g, 33.3 mmol) in thionyl chloride (15 ml) was heated at 40 degrees C. for 2 hours. The mixture was then concentrated and distilled in vacuo (boiling point 119 degrees C. at 20 mm Hg) to provide 3.58 g (60 percent yield by weight) of the acid chloride methyl ester. This was dissolved in 20 ml of dichloromethane and N-hydroxysuccinimide (2.75 g, 24.0 mmol) was added, followed by triethylamine (4.2 ml, 30 mmol). The mixture stirred for 10 minutes then diluted with ethyl acetate and washed with 0.5 M HCL and brine. The solution was dried over anhydrous magnesium sulfate, filtered and concentrated to give 4.5 g (87.5 percent yield by weight) of methyl succinimidyl adipate) as a colorless oil.

Proton NMR (in CDCl₃): delta 3.73 (singlet, 3H); delta 2.90 (singlet 4H), delta 2.70 (multiplet, 2H), delta 2.37 (multiplet, 2H), and delta 1 79 (multiplet 4H).

A solution of methyl succinimidyl adipate (4.5 g, 17.5 mmol), chlorotrimethylsilane (11.1 ml, 87.5 mmol) and sodium iodide (13.1 g, 87.5 mmol) in 10 ml of acetonitrile was heated at reflux for 12 hours. The mixture was then cooled to room temperature and diluted with ethyl acetate. The reaction mixture was washed repeatedly with 5 percent aqueous sodium bisulfite until the organic solution was colorless. Then it was washed with brine, dried over anhydrous magnesium sulfate, filtered and concentrated to provide 3.2 g (71 percent yield by weight) of adipic acid monosuccinimidyl ester as a white solid.

Proton NMR (in CDCl₃): delta 3.90 (singlet, 4H), delta 2.70 (multiplet, 2H), delta 2.4 (multiplet, 2H), delta 1.80 (multiplet, 4H).

A mixture of adipic acid succinimidyl ester (1.00 g, 3.80 mmol) and thionyl chloride (5 ml) was heated at 40 degrees C. for 3 hours, then cooled to room temperature and concentrated in vacuo. The residue was stirred several times with dry hexane, the oil was separated and dried in vacuo to provide 0.97 g (90 percent yield by weight) of succinimidyl adipoyl chloride. This was dissolved in dry tetrahydrofuran to make a 5 Molar solution, which was used as such in the preparation of compounds suitable for coupling to protein carriers.

Proton NMR (in CDCl₃): delta 3.00 (multiplet, 2H), delta 2.90 (singlet, 4H), delta 2.70 (multiplet, 2H), delta 1 80 (multiplet 4H).

Protein conjugates with phosphonate Compounds 1 and 4 are prepared by the addition of 0.5 milliliters (ml) of a solution of the phosphonate in cold water (2 milligrams (mg)/ml) to 1.0 ml of a solution of protein (KLH or BSA, 5 mg/ml) in sodium phosphate buffer (pH 7.2, 0.2 M) and stirring gently for two hours at 4 degrees C.

The introduction of a trifluoroacetyl group to the aminobenzylphosphonate of Compounds 1-4 simplifies further synthetic steps in which the phosphonyl chloride is required The dipicolinic acid moiety of compounds 3 and 4 provides an additional binding interaction between an antibody and the phenolic portion of these structures.

Nitrophenyl esters of p-trifluoroacetamidobenzylphosphonates are useful as intermediates in the scheme for coupling the haptens to carrier proteins by reduction of the nitro group to an amine function and acylation of this with a heterobifunctional adipic acid derivative such as succinimidyl adipoyl chloride, as described herein. The N-hydroxysuccinimidyl activated ester moiety in the phenolic ring (Compounds 2 and 4) allows efficient coupling to carrier proteins (KLH or BSA) in aqueous buffer solutions.

Succinimidyl glutaroyl chloride was similarly prepared and utilized.

IV. Preparation of Conjugates and Inocula

Conjugates of haptenic analog-ligand molecules with protein carriers such as keyhole limpet hemocyanin (KLH) can be prepared, for example, by activation of the carrier with a coupling agent such as MBS (m-maleimidobenzoyl-N-hydroxy succinimide ester), and coupling to the thiol group of the analog-ligand. See, for example, Liu et al., *Biochem.*, 80, 690 (1979). As is also well known in the art, it is often beneficial to bind a compound to its carrier by means of an intermediate, linking group.

Useful carriers are well known in the art and are generally proteins themselves. Exemplary of such carriers are keyhole limpet hemocyanin (KLH), edestin, thyroglobulin, albumins such as bovine serum albumin or human serum albumin (BSA or HSA, respectively), red blood cells such as sheep erythrocytes (SRBC), tetanus toxoid, cholera toxoid as well as polyamino acids such as poly(D-lysine:D-glutamic acid), and the like.

The choice of carrier is more dependent upon the ultimate intended use of the antigen than upon the determinant portion of the antigen, and is based upon criteria not particularly involved in the present invention. For example, if the conjugate is to be used in laboratory animals, a carrier that does not generate an untoward reaction in the particular animal should be selected.

The carrier-hapten conjugate is dissolved or dispersed in an aqueous composition of a physiologically tolerable diluent such as normal saline, PBS, or sterile water to form an inoculum. An adjuvant such as complete or incomplete Freund's adjuvant or alum can also be included in the inoculum. The inoculum is introduced as by injection into the animal used to raise the antibodies in an amount sufficient to induce antibodies, as is well known.

Exemplary immunogenic conjugates were prepared from the phosphonate esters by adapting their syntheses to incorporate a straight chain of carbon atoms on the phenolic group (alcohol portion of the analog-ligand ester) as a spacing element. Other exemplary immunogenic conjugates were prepared from phosphonamides by adapting these syntheses to incorporate the straight chain of carbon atoms on the acid portion of the analog-ligand as a spacing element. It was concluded that the flexible carbon chain of an adipate or glutarate appendage would reduce any bias to immunoreactivity due to the conformational constraint imposed by covalent attachment to the carrier protein. The bifunctional reagent prepared for this purpose also delivers the preactivated carboxyl group for linkage via amide bond formation with the lysine residues of the carrier. The particular coupling method used in this study is further described herein. The phosphonate esters were coupled to keyhole limpet hemocyanin (KLH) through an amino group of the phenolic portion of the structure.

According to the present invention, the intermediate linking agent is preferably succinimidyl adipoyl or glutaroyl chloride which was prepared as follows.

V. Preparation of Monoclonal Receptors

The foregoing KLH conjugates were used to immunize mice (129G1X+strain), and monoclonal antibodies were obtained as described by Niman et al., *Proc. Natl. Acad. Sci. USA*, 77, 4524 (1980) and Niman et al., in *Monoclonal Antibodies and T-Cell Products*, ed., Katz, D. H., 23-51 (CRC Press, Boca Raton, Fla. 1982). The lymphocytes employed to form the hybridomas of the present invention may be derived from any mammal, such as a primate, rodent (e.g., mouse or rat), rabbit, guinea pig, cow, dog, sheep, pig or the like As appropriate, the host may be sensitized by injection of the immunogen, in this instance a haptenic analog-ligand, followed by a booster injection, and then isolation of the spleen.

It is preferred that the myeloma cell line be from the same species as the lymphocytes. Therefore, fused hybrids such as mouse-mouse hybrids [Shulman et al., *Nature*, 276, 269 (1978)] or rat-rat hybrids [Galfre et al., *Nature*, 277, 131 (1979)] are typically utilized. However, some rat-mouse hybrids have also been successfully used in forming hybridomas [Goding, "Production of Monoclonal Antibodies by Cell Fusion," in *Antibody as a Tool*, Marchalonis et al. eds., John Wiley & Sons Ltd., p. 273 (1982)]. Suitable myeloma lines for use in the present invention include MPC-11 (ATCC CRL 167), P3X63-Ag8.653 (ATCC CRL 1580), Sp2/0-Ag14 (ATCC CRL 1581), P3 X 63 Ag8U.1 (ATCC CRL 1597), Y3-Agl.2.3. (deposited at Collection Nationale de Cultures de Microorganisms, Paris, France, number I-078) and P3X63Ag8 (ATCC TIB 9). The non-secreting murine myeloma line Sp2/0 or Sp2/0-Ag14 is preferred for use in the present invention.

The hybridoma cells that are ultimately produced can be cultured following usual in vitro tissue culture techniques for such cells as are well known. More preferably, the hybridoma cells are cultured in animals using similarly well known techniques with the monoclonal receptors being obtained from the ascites fluid so generated. The animals used for generation of the ascites fluid were female 129G1X$^{30}$ mice bred in the mouse colony of the Scripps Clinic and Research Foundation, La Jolla, Calif., however, when animals other than mice are used for preparation of the hybridomas, mice or that animal type can be used for the production of ascites fluid.

In particular, an exemplary monoclonal receptor was produced by the standard hybridoma technology of Kohler et al., *Nature*, 256, 495 (1975) Specifically, female 129G1X+ mice were immunized by intraperitoneal injection with an inoculum of 100 micrograms of conjugate (e.g., Compound 4i bound to KLH) in 300 microliters of a 1:1 mixture of phosphate buffered saline (PBS) pH 7.4 and complete Freund's adjuvant Two weeks later, the mice were again injected in a like manner with 50 micrograms of the foregoing conjugate in 300 microliters of a 1:1 mixture of PBS (pH 7.4) and 10 mg/ml alum. After an additional eight weeks, the mice were immunized intravenously with 50 micrograms of the conjugate in 200 microliters of PBS (pH 7.4). The spleens were removed from the mice 4 days later, and the spleen cells were fused to myeloma cells.

The spleens cells were pooled and a single cell suspension was made. Nucleated spleen cells ($1.4 \times 10^8$) were then fused with $3 \times 10^7$ Sp2/0 non-secreting myeloma cells in the presence of a cell fusion promoter (polyethylene glycol 2000). The hybridoma that produces a particular monoclonal antibody was selected by seeding the spleen cells in 96-well plates and by growth in Dulbecco's modified Eagle medium (DMEM) containing 4500 mg/liter glucose (10 percent), 10 percent fetal calf serum (FCS), hypoxanthine, aminopterin and thymidine (i.e., HAT medium) which does not support growth of the unfused myeloma cells.

After two to three weeks, the supernatant above the cell clone in each well was sampled and tested by an ELISA assay (enzyme linked immunosorbent assay as described hereafter) for the presence of antibodies against Compound 4. Positive wells were cloned twice by limiting dilution. Those clones that continued to produce Compound 4-specific antibody after two clonings were expanded to produce larger volumes of supernatant fluid. The hybridomas and the monoclonal receptors produced therefrom and described herein are identified by the laboratory designations "P3 6D4" and "P3 8D2", the particular material referred to being apparent from the context.

Two further catalytic monoclonal receptors were similarly prepared by another fusion using Compound 2i linked to an antigenic carrier as immunogen. Those two catalytic receptor molecules and their hybridomas were designated "P2 50D8" and "P2 57G4". Those two receptors were capable of catalytically hydrolyzing Compounds 5, 9 and 11. The evidence is presently unclear as to whether Compound 7 was catalytically hydrolyzed.

Thirty-two further hybridomas were similarly raised using Compound 13 as immunogen bound to KLH as antigenic carrier. About twenty-five molecules of Compound 13 were coupled per molecule of KLH, with a similar binding efficiency observed with BSA.

An immunogen should have a half-life of at least two days at an ambient blood pH value in order for immunization to occur. Previous studies [Bartlett et al., *J. Am. Chem. Soc.*, 103, 654 (1981)] had shown that alkylphosphonamidates can have a half-life of only minutes at a pH value range of 2-5, whereas at pH 8.5 stability appeared indefinite at a temperature of 5 degrees C. Compound 13 was found to have a half-life of eleven days at room temperature and a pH value of 7.3. No signs of decomposition were noted at pH values of 3.5 and 6.2.

Mice were hyperimmunized with the Compound 13-KLH conjugate over a three to four week time period. Sera were assayed in an ELISA using a Compound 13-BSA conjugate bound to microtiter plate wells as the solid-phase antigen. Cloned hybridomas were also screened using that ELISA assay.

Eight of the thirty-two monoclonal receptors that immunoreacted with Compound 13 catalytically hydrolyzed one or more reactant ligand esters. Each of those catalyses could be inhibited by an appropriate analog-ligand. Thus, a relatively high percentage of induced monoclonal receptors was capable of catalyzing an esterolytic reaction. The reason for this relatively high percentage of useful receptors being induced is unknown, but could be due to the presence of phosphonamidate group nitrogen atom, as compared to a phosphonate oxygen atom, or to the quinoline nucleus of the analog-ligand. Those eight catalytic monoclonal receptors and the hybridomas that secrete them are identified by the laboratory designations "QPN1 7E5", "QPN1 12C9", "QPN1 13E10", "QPN1 17G8", "QPN1 21G2", "QPN1 22F5", "QPN1 37G2" and QPN1 44A2. The prefix "QPNI" is sometimes omitted herein when discussing these hybridomas and receptors.

The hybridomas were deposited at the American Type Culture Collection 12301 Parkland Drive, Rockville, Md. as shown in the Hybridoma Deposit Table, below.

Hybridoma Deposit Table

| Hybridoma Designation Laboratory | ATCC | Deposit Date |
| --- | --- | --- |
| P3 6D4 | HB 9168 | August 6, 1986 |
| P3 8D2 | HB 9169 | August 6, 1986 |
| P2 50D8 | HB 9506 | August 18, 1987 |
| P2 57G4 | HB 9505 | August 18, 1987 |
| QPN1 7E5 | HB 9502 | August 18, 1987 |
| QPN1 12C9 | HB 9500 | August 18, 1987 |
| QPN1 13E10 | HB 9503 | August 18, 1987 |
| QPN1 17G8 | HB 9504 | August 18, 1987 |
| QPN1 21G2 | HB 9507 | August 18, 1987 |
| QPN1 22F5 | HB 9509 | August 18, 1987 |
| QPN1 37G2 | HB 9508 | August 18, 1987 |
| QPN1 44A2 | HB 9501 | August 18, 1987 |

The present deposits were made in compliance with the Budapest Treaty requirements that the duration of the deposits should be for 30 years from the date of deposit or for 5 years after the last request for the deposit at the depository or for the enforceable life of a U.S. patent that matures from this application, whichever is longer. The hybridomas will be replenished should they become non-viable at the depository.

Reference is often made herein to the use of receptors produced, raised or secreted from hybridoma P3 6D4. It will be understood, however, that comparable results can be and were obtained using receptors produced by hybridoma P3 8D2.

A monoclonal receptor of the present invention can also be produced by introducing, as by injection, the hybridoma into the peritoneal cavity of a mammal such as a mouse. Preferably, as already noted, syngenic or semi-syngenic mammals are used, as in U.S. Pat. No. 4,361,549, the disclosure of which is incorporated herein by reference. The introduction of the hybridoma causes formation of antibody-producing hybridomas after a suitable period of growth, e.g. 1-2 weeks, and results in a high concentration of the receptor being produced that can be recovered from the bloodstream and peritoneal exudate (ascites) of the host mouse Although the host mice also have normal receptors in their blood and ascites, the concentration of normal receptors is typically only about five percent that of the monoclonal receptor concentration.

The monoclonal receptor present in the hybridoma supernatant can be used without purification or the receptor can be recovered from the ascites or serum of the mouse using standard techniques such as affinity chromatography using AD 169-infected cells bound to an immunosorbant such Sepharose 6B or 4B (Pharmacia Fine Chemicals, Piscataway, N.J.), followed by elution from the immunosorbant using an acidic buffer such as glycine hydrochloride at a pH value of about 2.5.

In the present studies, IgG fractions were typically obtained from mouse ascites by precipitation with 45 percent saturated ammonium sulfate followed by chromatography on DEAE-Sephacel with sodium chloride elution. The fraction that was eluted with 100 mM salt was dialyzed and concentrated. Protein concentrations were determined by the Lowry method [*J. Biol. Chem.*, 193:265 (1951)]. The resulting concentrated solutions containing isolated IgG fractions were typically prepared into stock solutions of receptor at 20 mg/ml using Tris-HCl (50 mM, pH 6.5) for the receptors secreted from hybridomas P3 6D4 or P3 8D2, and at 4-5 mg/ml using 50 mM sodium phosphate (pH 8.0) containing 0.01 M sodium azide for the receptor secreted from hybridomas QPN1 7E5, QPN1 12C9, QPN1 13E10, QPN1 17G8, QPN1 21G2, QPN1 22F5, QPN1 37G2 and QPN1 44A2.

VI. Enzyme-linked Immunosorbent Assay (ELISA)

The binding of ligands and the effect of chemical modification were assayed by ELISA with antibody at fixed concentration in the range of its titer and varying reagent or ligand concentration. Inhibition is reported if the titer is reduced 50 percent at less than a 1000:1 ratio of reagent to hapten.

Assays were performed in flat-bottom polyvinyl microtiter plates (Dynatech, Alexandria, Va.). Illustratively, the wells were coated with a solution comprising Compound 4 bound to BSA as the antigen ligand in phosphate buffered saline (PBS) using 50 microliters of solution per well. Ligands were coated at 1 microgram per milliliter. The plates were then incubated overnight at 37 degrees C. in a dry oven. The dried plates were stored at 4 degrees C. until use. Prior to the ELISA assay, dried plates were rehydrated by two washes of 2 minutes each with 10 millimolar (mM) PBS, pH 7.4, containing 0.1 percent polyoxalkylene (20) sorbitan monolaurate (Tween 20) and 0.02 percent Thimerosal (sodium ethylmercurithiosalicylate), (Sigma, St. Louis, Mo.).

In order to reduce non-specific binding, hybridoma supernatants were diluted 1:2 in washing buffer containing 0.1 percent BSA as diluent. Fifty microliters of diluted hybridoma supernatants were thereafter added to each well and incubated for 1 hour at 4 degrees C. on a gyroshaker to contact the monoclonal antibody-containing supernatant with the bound Compound 4. Following two washes of 2 minutes each, 50 microliters of peroxidase-labeled goat anti-mouse IgG+IgM (Tago, Burlingame, Calif.), diluted 1:1000, were added to each well, and the reaction mixture was incubated at 4 degrees C. for 1 hour to bind the labeled antibody to bound monoclonal antibody.

The substrate used to assay bound peroxidase activity was prepared just prior to use and consisted of 400 microgram/ml o-phenylenediamine (Sigma, St. Louis, Mo.) in 80 mM citrate-phosphate buffer, pH 6.0, containing 0.12 percent $H_2O_2$. After two final washes, 50 microliters of substrate solution were added to each well, and color was allowed to develop for 15 minutes in the dark. Color development was stopped by adding 25 microliters of 4 molar (M) $H_2SO_4$ to each well and the optical density at 492 nanometers (nm) was measured with a Multiskan ELISA plate reader. Polyclonal antibodies raised to Compound 4i were observed to immunoreact (bind) to the analog-ligand, as did polyclonal antibodies raised to Compound 13 immunoreact with that analog-ligand.

VII. Hydrolytic Assays and Kinetic Measurements

Ester cleavage for reactant ligands such as Compounds 5 and 20 were determined by measuring the increase in fluorescence upon the production of 7-hydroxycoumarin and 4-methyl-7-hydroxycoumarin. A Perkin-Elmer LS-5 fluorescence spectrometer was operated at a fixed wavelength, using 355 nanometers (nm) for excitation and measuring the emission at 455 nm. A stock solution of the coumarin ester 5 was prepared in dioxane and was diluted to the desired concentrations in Tris-HCl (50 mM, pH 7) or sodium phosphate (50 mM, pH 4-9).

Reactions were run at 23 degrees C. and were initiated by the addition of an aliquot of antibody solution (1 mg/ml) to substrate solutions to provide a final protein concentration of 100 nM. Final fluorescence values were determined by hydrolysis of the substrate with pig liver esterase. The observed reaction rate was corrected for spontaneous hydrolysis. Reaction kinetics were studied by measuring initial rates under pseudo-first order conditions. Active protein concentration was extrapolated from fluorescence values at the end of the reaction. The kinetic parameters were obtained by fitting the data to a hyperbolic curve and from double reciprocal plots. Inhibition constants were determined from the Lineweaver-Burk plot data with at least five inhibitor concentrations. All the data were studied by a least squares analysis.

Amide cleavage for Compounds 14 and 15 was assayed by analyzing for the production of free aminoquinaldine or aminonaphthalene by measuring the increase in the azo dye that results from derivatizing the free aminoquinaldine or aminonapthalene with a diazotization reagent.

Catalysis reactions were conducted by preparing a reaction admixture of 100 microliters (ul) total volume containing 5 micromolar (uM) monoclonal antibody, 50-75 uM amide reactant ligand substrate and a buffer described hereinafter The buffer included in the above admixture varied depending upon the pH utilized as follows: pH 5, 10 micromolar (mM) sodium acetate, 10 mM sodium chloride; pH 7.2, 10 mM sodium phosphate, 0.15 molar (M) sodium chloride; pH 8.0; 50 mM sodium phosphate. The amide-containing substrates screened in this assay were added to the above admixture in 1 ul of a 100-fold concentrated stock solution of dimethyl formamide (DMF). Monoclonal antibody was added to the above admixture from a concentrated stock solution. The resulting admixture was placed into the well of a 96 well flat bottom microtiter plate (Costar, Cambridge, Mass.) and maintained in a moist vapor environment chamber at 23 degrees C. The production of aminoquinaldine or aminonaphthalene was then assayed as described below after 2,3,5, or 6 days.

The aminoquinaldine or aminonapthalene product produced by the catalyzed reaction was measured by first admixing 20 ul of 5 M HCl, 80 ul acetone and 10 ul 0.5% (w/v) sodium nitrite to the reaction admixture to form a second admixture and maintaining that second admixture for 3 minutes at room temperature. Thereafter, 10 ul 2.5% (w/v) ammonium sulfamate was added to form a third admixture that was maintained for 2 minutes at room temperature. A still further 10 ul of 0.5% (w/v) N-(1-napthyl)ethylenediamine dihydrochloride was added to form a fourth admixture that was then maintained for 15 minutes at room temperature. Thereafter the resulting azo dye present in the fourth admixture was measured by absorbance spectroscopy at 540 nanometers (nm) for aminoquinaldine using a Model EL 309 Automated Microplate Reader (Bio-Tek Instruments, Winooski, Vt.).

Using this assay, the presence of 10 uM aminoquinaldine could be observed with the naked eye. Nanomolar amounts could be detected with the automated microplate reader.

VIII. Protein Modification and Inactivation

Antibody preparations were inactivated without introducing fluorescent products by the addition of the activated ester (Compound 8) in dioxane to a solution of the IgG (5 mg/ml) in Tris-HCl (50 mM, pH 6.5) at a ratio of 5 moles of the ester (Compound 8) per mole IgG. The loss of activity was confirmed by reaction with the coumarin ester (Compound 5).

Protein modification was performed in an analogous manner, by the addition of a dioxane solution of the reagent at a known concentration to the antibody. The solution was incubated for 30 minutes before filtration through Sephadex G-25. The activity remaining was compared to control samples. Aliquots of IgG (5 mg/ml) inactivated with the ester (Compound 8) were diluted with four volumes of phosphate buffer (50 mM, pH 4–9, at intervals of 1 pH unit). Any pH change was recorded, and the sample was stored at 4 degrees C. for 24 hours. Activity was checked by dilution of each sample into 50 volumes of a solution of the coumarin ester (Compound 5) in 0.2 M phosphate buffer at pH 7, and the hydrolysis rate was compared with control samples.

IX. Monoclonal Antibodies Selected by Immunoassay and Esterolytic Assay

Although polyclonal receptors can be used, the present invention preferably employs monoclonal receptors. A monoclonal receptor provides a continuous source of a uniform immunoglobulin having a given specificity. Without monoclonal antibodies, obstacles are encountered, if only because the variability of an immune response, even within the same animal species, make it very difficult to reproduce results [C. Milstein, *Science,* 231, 1261 (1986)].

The strategy of this investigation was to generate as many unique clonal specificities as possible from a given immunization protocol and to initially select among these for immunoreactivity. Only those hybridoma cells producing antibodies of significant titer were considered for esterolytic assay. Thus, in a typical preparation, approximately 50–100 clones secreting anti-hapten antibody were initially identified in a particular fusion experiment using Compound 4i as immunogen. About two-thirds of these were not viable in cultures The remainder were subcloned and their isotype was determined. The hybridomas producing significant titer (greater than 1:64) IgG were propagated in ascites tumors to produce the antibody in large quantity [Niman et al., *Monoclonal Antibodies and T-Cell Products,* D. H. Katz, ed. (CRC, Boca Raton, Fla., 1982), pp. 23–51].

For fluorescence esterolytic assays, the substrate designed for the esterolysis assay was based on the large difference in fluorescence of 7-hydroxycoumarin or 4-methyl-7-hydroxycoumarin and their acylated derivatives. The fluorescence change upon hydrolysis of coumarin esters is easily detectable at nanomolar concentrations. The phenolic character of the coumarin ring allows it to be accommodated into the hapten binding site where a phenol derivative such as Compound 4i was used as immunogen or where a double-ringed compound such as a quinoline derivative like Compound 13 was used as immunogen.

The trifluoroacetamidophenyl acetyl ester behaved accordingly and exhibited fluorescence intensities at 455 nm (excitation at 355 nm) proportional to the extent of hydrolysis. The fluorescence intensity of 7-hydroxycoumarin is pH-dependent, increasing sharply above pH 7.0. The practical range of pH for the assay is limited by the rapid spontaneous rate of hydrolysis of an ester Compound 5 above pH 8.0. Initially, the ester was used at a concentration that was about four-fold than that of the protein, and the mixture was incubated at pH 7.2 for 10 minutes. Any change in fluorescence above background was noted.

In one study, twenty-eight monoclonal anti-hapten antibodies to phosphonate 2i from two separate fusion experiments were assayed. None of these were reactive with the coumarin ester (Compound 5) in the fluorescence assay. Antibodies to Compound 4i as hapten were assayed in the same manner. Twelve gamma-globulins were screened as described above. Compound 5 is homologous only in the acyl portion of this larger hapten; however, all but three of these cross-reacted with smaller phosphonate 2 in an ELISA assay as described herein. For two of these there was observed a fluorescence change, occurring in the first 5 minutes of incubation, which corresponds to about 50 percent of that for complete hydrolysis. The background rate of hydrolysis was reestablished after this initial reaction leveled off.

Thus, the simple ester Compound 5 was at least sufficient for the identification of these activities using the fluorescence technique. However, this does not rigorously identify the existence of other activities which may have narrow structural specificities that do not encompass the coumarin esters. This point was demonstrated for monoclonal receptor P3 6D4 by the following studies.

X. Monoclonal Receptor P3 6D4 Combining Site Directed Transacylation of Activated Esters A. Transacylation to Protein The nature of this antibody mediated esterolysis, including the specificity and the kinetics of the reaction, has been described above. The stoichiometry of the reaction and the chemical behavior of the products led to the hypothesis that a stable acylated antibody is formed from the transacylation of the ester to a nucleophilic group in the combining site.

The antibody-enhanced production of 7-hydroxycoumarin by esterolysis of acylated derivatives is unique for the trifluoroacetomidophenylacetyl Compound 5. The process is not detected with a coumarin ester having the apparently minor structural variation of a methyl group replacing the trifluoromethyl group of Compound 5. The reaction is presumably not defined by this leaving group since the reactive N-hydroxysuccinimide ester (Compound 6) will also specifically combine with the antibodies to produce an inactive product. The termination of the reaction is noted by the return of the rate of fluorescence increase to the background level. The net change in fluorescence is proportional to the amount of protein added. When this concentration is known independently from Lowry assay [Lowry et al., *J. Biol. Chem.*, 193, 265 (1951)] and the average molecular weight of an IgG is assumed to be 150,000, the stoichiometry is consistent with the reaction of one mole of ester per mole of combining sites. The reaction proceeds according to second order kinetics and the initial rate shows enzyme-like saturation.

Preliminary observations also included a pH-dependence of the rate. The modest rate increase at pH 8.0 versus pH 7.0 suggested the ionization of an active site base or nucleophile. Since an active protein was recovered by exposure of the inactive product to high pH values or hydroxylamine, this product was formulated as a chemically modified protein in which a specific residue of the combining site is acylated. The ability of the phosphonate analog-ligands (Compounds 1i and 3i) to block this reaction is shown in terms of their inhibition constants. The inhibition constants for the two inhibitors (Compounds 1i and 3i) were estimated at 100 nM and 35 nM, respectively, in the stoichiometric reaction with Compound 5. On the other hand, in the catalytic reaction observed with Compound 7, these compounds have inhibition constants $k_i$ of 0.80 micromolar (uM) and 0.16 uM, respectively.

Furthermore, the inactivation of the protein by tyrosine and histidine-specific reagents was noted. The haptens are also able to block this inactivation. It is not possible to distinguish between the existence of an acylimidazole or an acyltyrosine by treatment of the transacylation product with either tetranitromethane or diethylpyrocarbonate followed by deacylation at pH 9.0. The acylated protein is protected from irreversible inactivation by either reagent. This may simply mean that the covalent and non-covalent interactions of the acyl group are sufficient to impede both carboethoxylation of histidine and nitration of tyrosine in the combining site.

The original intent behind the use of the dipicolinic acid containing hapten was to determine if that ligand would be recognized immunologically as a metal chelate [Reardon et al., *Nature (London)*, 316, 265 (1985)]. Although no attempt was made to impose metal ion coordination upon the hapten-carrier conjugate as an immunogen, the possibility remained that an anti-hapten antibody might accept the chelate form. Thus, the effect of added picolinic acid and added zinc on the antibody-enhanced esterolysis with the coumarin reagent (Compound 5) was investigated. No effect on the primary reaction was observed with up to 100 micromolar added zinc and picolinic acid. The involvement of trace metal ions was excluded by the failure of added EDTA to affect the reaction.

The working hypothesis that was proposed for the transacylation mechanism takes into account the implications of histidine involvement and the apparently anomalous formation of a covalent bond between the reactant ligand and the antibody. Since no covalent mechanism is suggested by the phosphonate ester, the observed mechanism could represent a deviation from the expected mechanistic pathway which is a result of the particular choice of substrate used to study the activity. The catalytic role of histidine as a nucleophile in the transacylation would allude to the nucleophilic-/acid-base catalytic duality observed for imidazole [Bender et al., *The Bioorganic Chemistry of Enzymatic Catalysis*, p. 150, (Wiley, New York, 1984)]. For imidazole that mechanistic choice is determined by the basicity of the leaving group in the transacylation. In the context of an active site, where the imidazole is provided by the protein structure, this mechanistic alternative would be manifested as covalent or non-covalent catalysis by the enzyme. Demonstrating this required the modification of the ester substrate to change the basicity of the phenolate expelled in the reaction (the leaving group), while retaining the structural analogy correct for binding.

B Esterase Activity: Transacylation to Solvent

The leaving group structure suggested by the analog-ligand (or hapten) is the disubstituted phenolic ring with an abbreviated para-substituent to occupy the site of the coupling appendage. The acetamide group was used to replace this linkage in the free haptenic analog-ligand inhibitors (Compounds 1i and 3i). The analogous reactant ligand substrate would have the 2-picolinylcarboxamidomethyl-4-acetamidophenol as the alcohol portion of the ester.

As a first trial, the ester of 4-acetamidophenol (Compound 7), which is analogous to the phosphonate (Compound 1i), was prepared. The absence of the structurally significant ortho-substituent might diminish the binding potential of the ester, but should not drastically affect the chemical reactivity of the ester bond. The difference in binding may be assessed by comparing the inhibition constants of the phosphonate (Compounds 1i or 3i), which differ by this structural unit. As indicated in Section X(A), the inhibition constants for the two inhibitors (Compounds 1i and 3i) were estimated at 100 nM and 35 nM, respectively, in the stoichiometric reaction with Compound 5. In the catalytic reaction observed with (Compound 7), these compounds have inhibition constants $k_i$ of 0.80 micromolar and 0.16 micromolar, respectively. A binding contribution of perhaps an order of magnitude is due to this structure.

The lack of spectroscopic distinction between such esters and their hydrolysis products recommended a chromatographic analysis of the process. Referring to FIG. 3, a mixture of Compound 7 (5 uM) and the monoclonal antibody from hybridoma P3 6D4 (0.1 uM) in phosphate buffer (50 mM, pH 8.0) was analyzed over time by high performance liquid chromatography (HPLC). The accelerated hydrolysis of the ester was apparent from the decrease of its peak and the concurrent increase in two new peaks that correspond with the expected products. Under these conditions, the ester is completely consumed in 60-80 minutes during which time the background rate accounts for about 12 to 16 percent hydrolysis. The chormatographic profile is the same as that produced by treatment with hog liver esterase. Non-specific antibodies or anti-hapten antibodies which were inactive in the stoichiometric reaction with coumarin ester (Compound 5) do not demonstrate this ability.

The strict reactant ligand substrate specificity is noted by the failure to detect accelerated hydrolysis with aryl esters having diverse substitutional variations in the aromatic rings. With reference to Table 1, the succinylated ester. (Compound 8) was hydrolyzed by the receptor at a somewhat slower rate than the corresponding acetamide (Compound 7). This rate difference is also seen with hog liver esterase. It may represent the unfavorable electrostatics of the charged succinate interacting with the protein, or the disadvantage of a hydrophilic ligand binding to a hydrophobic antibody combining site, or in enzyme terminology, active site. Similar esters which are not accepted as substrates include Compound 9, that demonstrates the absolute requirement of the trifluoromethyl group, as was also observed in the stoichiometric reaction.

TABLE 1*

| Compound | t₁ (min) Antibody (P3 6D4) | Esterase | $k_{uncat}^c$ ($\times 10^5$ sec$^{-1}$) |
|---|---|---|---|
| 7 | 16 | 4 | 2.8 |
| 8 | 60 | 52 | 3.8 |
| 9 | a | 4 | 0.25 |
| 10 | a | 2$^b$ | 1.63 |
| 11 | a | 5 | 6.10 |

*Hydrolysis of carboxylic esters by monoclonal antibody (from hybridoma P3 6D4) and by hog liver esterase (Sigma Chemical Co., St. Louis, MO, EC 3.1.1.1) determined by HPLC on an analytical RP-C18 column (Vydac 218TP54) with isocratic elution [acetonitril: water plus 0.1 percent trifluoroacetic acid; (35:65)] at a flow rate of 1.0 ml/min and the detector set at 245 nm. The initial substrate concentration was 5 micromolar and that the internal standard (acetophenone) was 10 micromo lar in 50 mM phosphate buffer at pH 8.0. The retention times (minutes) were as follows: acetophenone, 5.0; Compound 7, 8.3; Compound 8, 6.7; Compound 9, 4.1; Compound 10, 11.1 (40 percent acetonitrile elution); Compound 11, 8.2. The antibody concentration was 15 micrograms/ml (0.1 micromolar) and that of esterase was 5.5 microgragms/ml. The reaction mixtures were kept at 25 degrees C and aliquots were analyzed at intervals of 2 to 20 minutes. Three or more determinations were used to plot a curve from which the half-life of the reaction is estimated (see FIG. 3).
$^a$The ester was not consumed faster than the background rate of hydrolysis.
$^b$The reaction is too rapid to be measured accurately by HPLC.
$^c$The rate constants were determined spectrophotometrically (at 245 nm) by measuring initial rates at five concentrations of ester.

More remarkable is the specificity imparted by the acetamido group of the phenol. The phenyl ester (Compound 10) is of approximately the same reactivity as 4-acetamidophenyl ester (Compound 7), and is more congruous with the haptenic structure than the coumarin ester (Compound 5). Yet here again, the receptor had no effect on the hydrolytic rate. The ester (Compound 11), in which the trifluoroacetyl and the acetyl groups of Compound 7 are interchanged, presents a unique option for inverted orientation of the ester bond in the binding site if the similarities of the phenolic and benzylic moieties allow this kind of interchange. Nevertheless, this possibility is not manifested by the accelerated hydrolysis of this ester. On the other hand, the hydrolysis of all these esters is accelerated by the indiscriminate esterase from hog liver. Chemical selectivity is a distinguishing feature of the catalytic antibody and can be considered a reflection of the exquisite binding specificity of immunological recognition.

It was desirable to prepare Compound 8 to show that the saturation velocity observed with Compound 7 was not a consequence of its limited solubility in aqueous buffer solutions. The succinylated ester (Compound 8) is readily soluble at concentrations up to 100 micromolar in phosphate buffer (50 mM, pH 8.0), whereas solutions of Compound 7 become slightly turbid at concentrations above 15 micromolar.

Reaction kinetics were measured spectrophotometrically by following the absorption change at 245 nanometers. The pseudo first-order rate shows enzyme-like saturation and, as shown in FIG. 4, and the phosphonate analog-ligands behave as competitive inhibitors in Lineweaver-Burk analyses. Kinetic parameters obtained with these substrates are shown in Table 2 along with the inhibition constants obtained with phosphate (Compound 3). Under these conditions, the acceleration above the background rate is about 960-fold for Compound 7 and about 200-fold for Compound 8 (corrected for the background hydrolysis rate).

TABLE 2*

| Compound | $K_m$ ($\times 10^6$M) | $K_i$ ($\times 10^7$M) | $V_{max}$ ($\times 10^9$M sec$^{-1}$) | $k_{cat}$ ($\times 10^2$ sec$^{-1}$) | $\dfrac{K_{cat}}{k_{uncat}}$ |
|---|---|---|---|---|---|
| 7 | 1.90 | 1.60 | 2.2 | 2.7 | 960 |
| 8 | 0.62 | 0.65 | 1.0 | 0.8 | 210 |

*The kinetic parameters shown in Table 2 are for the hydrolysis of esters (Compounds 7 and 8) by monoclonal antibody P3 6D4. A Perkin-Elmer lambda 4B spectrophotometer, equipped with thermostatted cell holder, was used to measure absorption changes at 245 nm. Cells containing the substrate at concentrations of 0.5 to 50 micromolar in phosphate buffer (50 mM, pH 8.0) were preequilibrated at 25 degrees C. The concentration of active IgG in a stock solution was found by reacting with the coumarin ester (Compound 5) and measuring the yield of hydroxycoumarin by fluorescence. The kinetic run was initiated by addition of an aliquot of the antibody stock solution (in 50 mM phosphate buffer, pH 8.0) calculated to give 100 nM IgG. The mixture was allowed to equilibrate for 2 to 3 minutes and the rate was then measured during the subsequent 10 minutes. The absorption change for complete hydrolysis was determined by treatment with esterase. Kinetic parameters were obtained from Lineweaver-Burk plots (see FIG. 4). Inhibition constants were determined from a plot of the slopes with at least four inhibitor concentrations of Compound 3. The data were analyzed by linear regression.

The pH values at which these measurements were made are most likely not optimal. Preliminary indications suggest that this reaction is more sensitive to pH value than the previously discussed transacylation with coumarin ester. The catalytic reaction is nearly undetectable at pH 7.0. Further kinetic studies may define the true rate acceleration with these substrates. A greater rate difference may be expected for an ester containing all the epitopes of the hapten including the picolinyl group.

Addition of picolinic acid or picolinic acid and zinc chloride to the reaction mixture of ester Compound 7 and the antibody had no effect on the observed rate. This suggests, but does not conclusively demonstrate, that the binding site may not simultaneously accommodate two fragments of the haptenic structure. That situation would be extremely important to identify, as it relates to the ability of enzymes to bind more than one substrate or a substrate and a cofactor simultaneously. The present situation presumably involves such an interaction where a water molecule is complementary to the ester in filling the binding site.

C. Nucleophilic Versus General
   Base Mechanism and Catalysis

Indications that a histidine is critical to the activities of the esterolytic antibodies provided the earliest clue regarding the mechanism of transacylation. The nucleophilic character of imidazole is well established. However, there is no evidence that enzymes employ the imidazole group of histidine for nucleophilic catalysis. On the other hand, the function of the imidazole group of histidine in general acid-base catalysis is widely appreciated in enzyme mechanisms [C. Walsh, *Enzymatic Reaction Mechanisms*, p. 43, (Freeman, San Francisco, 1979)].

The dual role of imidazole as a nucleophilic and general base catalyst is understood in terms of the mechanisms of ester hydrolysis. The transition between these mechanisms is determined by the relative rates of product formation from the two possible tetrahedral intermediates: that derived from addition of imidazole to the acyl group versus that from hydroxide addition. The relatively labile 7-hydroxycoumarin ester forms an imidazole adduct that can readily collapse to the acyl imidazole intermediate by loss of the coumarin alkoxide. This step becomes more difficult with poor leaving groups that form less stable alkoxides. The 7-hydroxycoumarin (pK$_a$ 8.3) is a substantially better leaving group than 4-acetamidophenol (pK$_a$ 9.9). The 4-acetamidophenyl ester Compound 5 may, therefore, form a tetrahedral adduct with water or hydroxide whose breakdown is presumably catalyzed (see FIG. 5).

As evidence for the existence of separate mechanisms, it was determined that the product of the reaction of the antibody combining site with Compound 5 is not an intermediate in the catalytic reaction with Compound 7. Indeed, Compound 5 acts as a specific inactivator of the catalyst when it is added to a mixture of the receptor and Compound 7. The two esters are differentiated with considerable fidelity, as the receptor is observed to turn over several hundred fold with substrate Compound 7 without noticeable inactivation. Catalysis by the receptor through both mechanisms implies that the binding interactions can stabilize either transition state in these two-step processes. However, for the design intent only, the general base process is relevant, where the second step (break down to products) is rate limiting.

The contribution of binding to catalysis via this general base mechanism is best illustrated by the different behavior of the 4-acetamidophenyl ester (Compound 7) and the simple phenyl ester (Compound 10). Phenol as a leaving group (p$K_a$ 9.89) is equivalent to 4-acetamidophenol, yet the hydrolysis of Compound 10 is not catalyzed by receptor P3 6D4. Neither is the stoichiometric reaction apparent although Compound 10 has the correct structure for the acyl group.

Therefore, although this ligand may bind to the protein, the interaction is not proper for the expression of the inherent esterase function. The effect of binding to the acetamide group of Compound 7 is sufficient to stabilize the rate limiting transition state, or alternatively destabilize the tetrahedral intermediate relative to that transition state.

Further refinement of the substrate structure, as in the addition of the picolinate substituent, will reveal the full extent of the binding interactions in catalysis. In this system, there is the disadvantage that the low $K_M$ values may eventually overwhelm the contribution of additional binding interactions to catalysis. The transition state complementarity criterion can assure that $k_{cat}/K_M$ will tend to be maximized, while at a given value of $k_{cat}/K_M$ the maximization of the rate ($k_{cat}$) depends on the poor binding of substrate (high $K_M$) [A. Fersht, *Enzyme Structure and Mechanism*, 2nd ed., pages 311–346, (Freeman, San Francisco, 1985)].

XI. Transacylations Directed by Combining Sites of Eight Additional Monoclonal Receptors A. Reactivity with Reactant Ligands A variety of catalytic activities are exhibited by the eight monoclonal receptors denominated 21G2, 7E5, 37G2, 13E10, 12C9, 44A2, 17G8 and 22F5. This variety is exhibited both in regard to the reactant ligand substrates whose hydrolysis they catalyze, and the rates of hydrolysis observed relative to the spontaneous, background hydrolytic rates of those reactant ligand substrates. Preliminary relative reactivities for ten substrates are shown in Table 3, below.

TABLE 3

Hydrolyses by Monoclonal Receptors with Various Reactant Ligands[1]

| Concentrations[2] | | | | | Monoclonal Receptors | | | | | | |
|---|---|---|---|---|---|---|---|---|---|---|---|
| Rec. | Lig. | Lig.[3] | Time[4] | Spon.[5] | 21G2 | 37G2 | 13E10 | 1209 | 44A2 | 17G8 | 22F5 |
| — | — | 14 | — | — | — | — | — | — | — | — | — |
| — | — | 15 | — | — | — | — | — | — | — | — | — |
| — | — | 16 | — | — | — | — | — | — | — | — | — |
| 1 | 10 | 17[6] | 2 | 4 | 10 | 35 | 39 | 33 | 35 | 19 | 15 | 16 |
| 1 | 10 | 17 | 2 | 7 | 10 | 30 | 60 | 32 | 55 | 62 | NT | 51 |
| 2 | 10 | 18 | 24 | 34 | 72 | 76 | 92 | 69 | 56 | 84 | 84 | 100 |
| 2 | 5 | 19 | — | — | — | — | — | — | — | — | — |
| 2 | 10 | 20 | 0.33 | 14 | 36 | 15 | 39 | 16 | 16 | 33 | 20 | 48 |
| 1 | 5 | 5 | 0.33 | 5 | 43 | 8 | 12 | 13 | 11 | 47 | 16 | 48 |
| 5 | 10 | 21 | — | — | — | — | — | — | — | — | — |
| 5 | 10 | 22 | 3.5 | 5 | 19 | 9 | 45 | 14 | 12 | 24 | 22 | 26 |

[1]Preliminary initial hydrolyses shown as the percentage of admixed reactant ligand consumed for catalyzed and spontaneous hydrolyses. "—" = No hydrolysis observed. All reactions were carried out at pH 8.0 in a 50 mM phosphate buffer unless otherwise noted. Hydrolytic percentages were determined by HPLC using a Hitachi model 655A-12 liquid chromatograph with a C18 Vydac 201TP54 column, except as noted below. Mixtures of acetonitrile and water containing 0.1 percent trichloroacetic acid [28:72–50:50 (v/v)] were used as elutant. Hydrolyses of Compounds 5 and 20 were assayed using fluorescence data.
[2]Concentrations of receptor molecules (Rec.) and reactant ligands (Lig.) in micromolar units, presuming a molecular weight of 150,000 daltons for each receptor molecule.
[3]Reactant ligand (Lig.) used as substrate.
[4]Time in hours that the reaction was permitted to take place.
[5]Spontaneous hydrolytic percentages for the time period indicated.
[6]Reaction carried out at pH 7.2 in a 50 mM phosphate buffer.

Correlation of catalyzed hydrolytic reactivity with the structures of the reactant ligands used as substrates reveals several features.

First, each of the eight monoclonal receptors turned over and catalyzed the hydrolysis of more than a stoichiometric amount (relative to the receptor concentrations) of reactant ligand in the above or other studies. Thus, a relatively stable intermediate analagous to that formed from Compound 5 reacted with receptor 3P 6D4 did not form with any of these eight receptor molecules, regardless of the pKa value of the alcohol portion of the ester reactant ligand.

Second, a two-ringed alcohol portion of the ester reactant ligand was preferred over a single ring since all of the receptors catalyzed hydrolysis of Compounds 17 and 5 that contained alpha-naphthoxy and coumarinoxy esters, whereas five of eight and none of the receptors catalyzed hydrolysis of Compounds 22 and 19, respectively, that contained phenoxy and methoxy esters.

Third, a phenyl ring bonded to an oxygen that is itself bonded to the central atom, a carbonyl carbon in the reactant ligands, appears to be a predominant epitope recognized since all of the receptors except 12C9 catalyzed the hydrolysis of Compound 18 that had a hydrogen in place of the ring in the acid portion of the ester, and five of eight of the receptors catalyzed hydrolysis of the phenoxy ester, Compound 22. Only those same five receptors also catalyzed hydrolysis of the 4-methylcoumarinoxy ester, Compound 20.

Fourth, none of the receptors catalyzed hydrolysis of either of the amides, Compounds 14 and 15. The reason for that lack of reactivity is unknown and is being examined.

Fifth, reactant ligand substrates having a nitrogen atom gamma from the oxygen atom of the alcohol portions of the ester reactant ligands failed to react; i.e., Compounds 16 and 22. This was surprising in view of the excellent reactivity exhibited by the isostructural coumarinoxy ester and the similarly structured alpha-naphthalenoxy ester.

The reason that reactant ligand substrates with a nitrogen atom gamma to the alcohol portion alcohol atom are not catalytically hydrolyzed is unknown. One possibility is that the nitrogen atom of the reactant ligand (Compound 16 or analog-ligand, here, Compound 13) was positively charged at pH values utilized and an amino acid residue of the receptor molecule combining site is positioned to stabilize it. That mechanism would not, however take into account the lack of hydrolysis of Compound 21 whose gamma nitrogen is a portion of an amide that should not be effected by the stabilization provided to a charged nitrogen atom.

Another possibility that accounts for the reactivity of both of Compounds 16 and 21 is that the lone pair of electrons on a gamma nitrogen is stabilized by a receptor molecule combining site amino acid residue such as a carboxyl group of an aspartic or glutamic acid, an imidazole of a histidine residue, or a mercaptan of a cysteine When a gamma nitrogen is present, the stabilizing group tends to inhibit hydrolysis, whereas when the gamma nitrogen is absent the former stabilizing group can assist in the hydrolytic reaction. Assistance in enzyme-catalyzed hydrolytic reactions is well documented for carboxyl, imidazole and mercaptan groups.

B. Kinetics Studies

Reaction kinetics were studies using three reactant ligands as substrates for monoclonal receptors 37G2 and 22F5. Data from initial rates were consistent with Michaelis-Menten reaction mechanism for a usual enzyme-substrate system. Initial rates were followed using at 271 mn using a U.V.-visible spectorphotometer for Compound 17, and a fluorescence spectrometer for Compounds 5 and 20, using an excitation wavelength of 355 nm and an emmision wavelength of 455 nm for both compounds.

Lineweaver-Burke plots for the catalyzed hydrolysis of Compounds 17, 5 and 20 obtained in the presence and absence of Compound 12i as inhibitor were prepared as discussed for FIG. 4. In particular, Compound 17 was present at concentrations of 2-16 uM with inhibitor concentrations of 100 and 300 nanomolar (nM). Compound 5 was present at concentrations of 1-10 uM with inhibitor concentrations of 100 and 200 nM. Compound 20 was present at concentrations of 2-20 uM with inhibitor concentrations of 25 and 100 nM. The kinetic parameters derived from those plots are shown in Table 4, below.

TABLE 4*

| $K_m$ ($\times 10^6$M) | $K_i$ ($\times 10^7$M) | $V_{max}$ ($\times 10^9$Msec$^{-1}$) | $K_{cat}$ (sec$^{-1}$) | $K_{uncat}$ ($\times 10^6$ se$^{-1}$) |
|---|---|---|---|---|
| Monoclonal Receptor 37G2 and Compound 17 | | | | |
| 15 | 1.4 | 0.77 | 0.0016 | 9.29 |
| Monoclonal Receptor 22F5 and Compound 20 | | | | |
| 5 | 0.7 | 4.5 | 0.023 | 19.3 |
| Monoclonal Receptor 22F5 and COmpound 5 | | | | |
| 1.4 | 1.1 | 1.52 | 0.0022 | 42.6 |

*Fluorescene assays using Compounds 20 and 5 were carried out in a Perkin-Elmer fluorescene spectrophotometer (moded LS-5; Oakbrook, IL) using 200 nanomolar receptor (based on a molecular weight of 150,000 daltons) in 50 mM phosphate buffer at a pH value of 8.0. The reactant ligand was dissolved in dioxane and admixed in the amounts discussed above. Two milliliters of reaction solution were utilized as was a dioxane concentration of 2 percent by volume. Assays with Compound 17 as reacta nt ligand utilized 500 nanomolar receptor (based on a molecular weight of 150,000 daltons) in the above buffer, using the reactant ligand dissolved in dioxane and a total dioxane concentration of 2 percent by volume.

As can be seen from Table 4, the kinetic parameters obtained from these studies were generally similar to those shown in Table 2. Interestingly, however, the leaving group effect noted with receptor P3 6D4 was not noted with either receptor of Table 4. Thus, receptor P3 6D4 appeared to form a relatively stable N-acyl histidine with the 7-hydroxycoumarin ester (pK$_a$ of coumarin about 8.3) presumably by a nucleophilic mechanism of hydrolytic cleavage, whereas that receptor appeared to catalyze hydrolytic cleavage by a general base mechanism for an ester whose leaving group (p-acetamidophenol) had a higher pK$_a$ value (about 9.9). Here, a relatively stable intermediate was not formed, and each of the three catalytic hydrolyzes appeared to proceed by a transition state rather than by intermediate formation. In addition, reactant ligands having leaving group alcohol portions, alpha-naphthol and coumarin derivatives, with pK$_a$ vaues of about 9.3 and about 8.3, exhibited similar K$_{cat}$ values with each of the monoclonal receptors studied. For Compounds 17 and 5 used as reactant ligands with monoclonal receptors 37G2 and 22F5, the observed differences in acceleration due to the catalyzed reaction were mainly a function of the spontaneous, uncatalyzed rate, which was about a factor of four faster for the ester whose alcohol has the lower pK$_a$ value.

XII. Discussion

The transition state analog designation is accepted cautiously in the study of enzymes since neither the catalytic mechanisms nor the interaction of the enzymes with these ligands is well understood in most cases. A detailed inquiry will often precede a definitive claim to such a title [Bartlett et al., Biochemistry, 22, 4618 (1983) and Imperali et al., Biochemistry, 25, 3760 (1986)].

As described herein, the phosphonate structure has earned this identity by definition, since it is associated with the understanding of the chemical reaction mechanism. By exacting the expected function in an immunological receptor, it fulfills its purpose and provides persuasive evidence for the theoretically derived principle of enzyme-transition state complementarity. That ability is unique and independent of the physiological origins of enzymic catalysis. This has particular significance as the study of "enzyme-like" catalysis need not be subservient to the discrete chemistry exalted by natural enzymes. The catalysis of any reaction for which a credible mechanism can be formulated may be given attention.

The direction and focus of further work on enzyme systems is not dependent on a detailed understanding of existing enzymes. However, the work of natural enzymes must always be regarded as the paradigm of catalysis. Much useful information from the study of enzyme mechanisms can be brought to bear on designs for artificial catalysis. Enzymes in their incipient form are nothing but specialized protein molecules, as are monoclonal antibodies of unique specificity. Proteins alone cannot exhibit all the chemistry of life processes. Organisms have, therefore, evolved to import extracellular components which combined with proteins form the vast array of enzymic activities. For enzymes to aspire to that range of chemical reactions they must be provided with cofactors. Attempting to encompass metal chelation in transition state binding is one example of such a scheme. Cofactors found in nature should be valuable models for defining systems in which immunological binding may be brought to bear on the catalysis of oxidative, electron transport, or hydride transfer activity, for example.

Techniques for obtaining antibodies of desirable specificities have led to a broad range of applications in medicine and biology. These all use the common function of antigenic recognition in some coupled manner to associate other activities or properties with the antibody-antigen complex. The simple binding interaction is thought to be an invariant property of antibodies.

In these studies, the knowledge of chemical mechanisms has been used to harness the potential energy of antibody-antigen binding to perform a new, kinetic function. The success of this basic inquiry should encourage the application of mechanistic design to invoke more interesting and perhaps useful proteins from the immune system. The ability to impart hydrolytic activity to antibodies of predetermined specificity suggests that site-specific reagents or catalysts can be created at will. Aside from the fundamental interest of that prospect, it can have enormous practical benefit to protein chemistry.

The foregoing is intended as illustrative of the present invention but not limiting. Numerous variations and modifications may be effected without departing from true spirit and scope of the invention.

What is claimed is:

1. Monoclonal antibody molecules or antibody combining site-containing portions thereof that catalytically hydrolyze a preselected ester bond of a reactant ligand, said antibody combining site binding:
   (a) to said reactant ligand having said preselected ester bond; and
   (b) to and induced by an analog of said ligand having a tetrahedrally bonded phosphorus atom located at the position occupied by the carbonyl carbon of said preselected ester bond of said ligand, said tetrahedrally bonded phosphorus atom being bonded directly to:
   (i) the alpha-carbon atom of the acid portion of said analogous ligand ester;
   (II) two oxygen atoms, one of which is doubly bonded to said phosphorus atom, and the other of said two oxygen atoms is bonded singly to said phosphorus and singly to a radical selected from the group consisting of hydrogen and $C_1$-$C_4$ lower alkyl; and
   (iii) a third oxygen atom that is bonded to the alpha-carbon atom of the alcohol portion of said analogous ester.

2. The monoclonal molecules of claim 1 secreted by the hybridoma P3 6D4 having ATCC accession number HB 9168.

3. The monoclonal molecules of claim 1 secreted by the hybridoma P3 8D2 having ATCC accession number HB 9169.

4. The monoclonal molecules of claim 1 secreted by the hybridoma P2 50D8 having ATCC accession number HB 9506.

5. The monoclonal molecules of claim 1 secreted by the hybridoma P2 57G4 having ATCC accession number HB 9505.

6. The monoclonal molecules of claim 1 secreted by the hybridoma QPNI 7E5 having ATCC accession number HB 9502.

7. The monoclonal molecules of claim 1 secreted by the hybridoma QPNI 12C9 having ATCC accession number HB 9500.

8. The monoclonal molecules of claim 1 secreted by the hybridoma QPNI 13E10 having ATCC accession number HB 9503.

9. The monoclonal molecules of claim 1 secreted by the hybridoma QPNI 17G8 having ATCC accession number HB 9504.

10. The monoclonal molecules of claim 1 secreted by the hybridoma QPNI 17G2 having ATCC accession number HB 9507.

11. The monoclonal molecules of claim 1 secreted by the hybridoma QPNI 22F5 having ATCC accession number HB 9509.

12. The monoclonal molecules of claim 1 secreted by the hybridoma QPNI 37G2 having ATCC accession number HB 9508.

13. The monoclonal molecules of claim 1 secreted by the hybridoma QPNI 44A2 having ATCC accession number HB 9501.

14. A method of catalytically hydrolyzing a preselected ester bond in a reactive ligand molecule comprising the steps of:
   (a) admixing an effective amount of the monoclonal antibody molecules or antibody combining site-containing portions thereof of claim 4 with said reactant ligand molecules in an aqueous medium to form an admixture; and
   (b) maintaining said admixture for a period of time sufficient for said ligand molecules to bind to said monoclonal antibody molecules or antibody combining sitecontaining portions thereof and for said monoclonal antibody molecules or antibody combining site-containing portions thereof to hydrolyze said preselected bond.

15. The method of claim 14 including the further step of recovering the products of said hydrolysis.

16. Monoclonal antibody molecules or antibody combining site-containing portions thereof that hydrolyze a preselected ester bond of a reactant ligand, said antibody combining site binding:
   (a) to said reactant ligand having said preselected ester bond; and
   (b) to and induced by an analog of said ligand having a tetrahedrally bonded phosphorus atom located at the position occupied by the carbonyl carbon of said preselected ester bond of said ligand, said tetrahedrally bonded phosphorus atom being bonded directly to:
   (i) the alpha-carbon atom of the acid portion of said analogous ligand ester;
   (II) two oxygen atoms, one of which is doubly bonded to said phosphorus atom, and the other of said two oxygen atoms is bonded singly to said phosphorus and singly to a radical selected from the group consisting of hydrogen and $C_1$-$C_4$ lower alkyl; and (iii) a third oxygen atom that is bonded to the alpha-carbon atom of the alcohol portion of said analogous ester.

17. Antibody molecules or antibody combining site-containing portions thereof that catalytically hydrolyze a preselected ester bond of a reactant ligand, said antibody combining site binding:
 (a) to said reactant ligand having said preselected ester bond; and
 (b) to and induced by an analog of said ligand having a tetrahedrally bonded phosphorus atom located at the position occupied by the carbonyl carbon of said preselected ester bond of said ligand, said tetrahedrally bonded phosphorus atom being bonded directly to:
   (i) the alpha-carbon atom of the acid portion of said analogous ligand ester;
   (II) two oxygen atoms, one of which is doubly bonded to said phosphorus atom, and the other of said two oxygen atoms is bonded singly to said phosphorus and singly to a radical selected from the group consisting of hydrogen and $C_1$–$C_4$ lower alkyl; and
   (iii) a third oxygen atom that is bonded to the alpha-carbon atom of the alcohol portion of said analogous ester.

18. Antibody molecules or antibody combining site-containing portions thereof that hydrolyze a preselected ester bond of a reactant ligand, said antibody combining site binding:
 (a) to said reactant ligand having said preselected ester bond; and
 (b) to and induced by an analog of said ligand having a tetrahedrally bonded phosphorus atom located at the position occupied by the carbonyl carbon of said preselected ester bond of said ligand, said tetrahedrally bonded phosphorus atom being bonded directly to:
   (i) the alpha-carbon atom of the acid portion of said analogous ligand ester;
   (II) two oxygen atoms, one of which is doubly bonded to said phosphorus atom, and the other of said two oxygen atoms is bonded singly to said phosphorus and singly to a radical selected from the group consisting of hydrogen and $C_1$–$C_4$ lower alkyl; and
   (iii) a third oxygen atom that is bonded to the alpha-carbon atom of the alcohol portion of said analogous ester.

* * * * *

UNITED STATES PATENT AND TRADEMARK OFFICE
CERTIFICATE OF CORRECTION

PATENT NO.   : 5,030,717
DATED        : July 9, 1991
INVENTOR(S)  : Alfonso Tramontano, Kim Janda and Richard A. Lerner It is certified that error appears in the above-identified patent and that said Letters Patent is hereby corrected as shown below:

Column 1,
Line 6, insert -- This invention was made with government support under Grant No. GM 35318 from the National Institutes of Health. The U.S. government may have certain rights in the invention. --

Signed and Sealed this

Fourth Day of June, 2002

Attest:

Attesting Officer

JAMES E. ROGAN
Director of the United States Patent and Trademark Office